(12) United States Patent
Chen

(10) Patent No.: US 12,166,069 B2
(45) Date of Patent: Dec. 10, 2024

(54) SEMICONDUCTOR DEVICE AND MANUFACTURING METHOD THEREOF

(71) Applicants: TAIWAN SEMICONDUCTOR MANUFACTURING CO., LTD., Hsinchu (TW); TSMC CHINA COMPANY LIMITED, Shanghai (CN)

(72) Inventor: Zheng-Long Chen, New Taipei (TW)

(73) Assignees: TAIWAN SEMICONDUCTOR MANUFACTURING CO., LTD., Hsinchu (TW); TSMC CHINA COMAPNY LIMITED, Shanghai (CN)

( * ) Notice: Subject to any disclaimer, the term of this patent is extended or adjusted under 35 U.S.C. 154(b) by 0 days.

(21) Appl. No.: 18/351,149

(22) Filed: Jul. 12, 2023

(65) Prior Publication Data

US 2023/0352305 A1 Nov. 2, 2023

Related U.S. Application Data

(60) Continuation of application No. 17/666,386, filed on Feb. 7, 2022, now Pat. No. 11,742,207, which is a (Continued)

(30) Foreign Application Priority Data

Mar. 17, 2020 (CN) .......................... 202010186664.7

(51) Int. Cl.
*H01L 29/06* (2006.01)
*H01L 21/04* (2006.01)
(Continued)

(52) U.S. Cl.
CPC .......... *H01L 29/06* (2013.01); *H01L 21/0415* (2013.01); *H01L 21/046* (2013.01);
(Continued)

(58) Field of Classification Search
CPC ..... H01L 29/06; H01L 29/0684; H01L 29/36; H01L 29/1079; H01L 29/4236;
(Continued)

(56) References Cited

U.S. PATENT DOCUMENTS

2002/0125529 A1 9/2002 Zeng
2003/0062569 A1* 4/2003 Letavic ............... H01L 29/7813
257/E21.345

(Continued)

FOREIGN PATENT DOCUMENTS

JP 2005229066 A 8/2005
JP 2012238834 A 12/2012

*Primary Examiner* — Joseph C. Nicely
(74) *Attorney, Agent, or Firm* — Maschoff Brennan

(57) ABSTRACT

A semiconductor device includes substrate, a first gate structure, a second gate structure, and an epitaxy layer. The first gate structure and the second gate structure are over the substrate, in which the first gate structure and the second gate structure each comprises a shielding electrode, a gate electrode over the shielding electrode, and a first gate dielectric layer vertically separating the shielding electrode from the gate electrode. The epitaxy layer is over the substrate and cups an underside of the first gate structure and the second gate structure, in which the epitaxy layer comprises a doped region laterally between the first gate dielectric layer of the first gate structure and the first gate dielectric layer of the second gate structure, a dopant concentration of the doped region being non-uniform along a lateral direction.

20 Claims, 28 Drawing Sheets

Related U.S. Application Data division of application No. 16/859,840, filed on Apr. 27, 2020, now Pat. No. 11,244,830.

(51) Int. Cl.

| | |
|---|---|
| *H01L 21/225* | (2006.01) |
| *H01L 21/265* | (2006.01) |
| *H01L 21/266* | (2006.01) |
| *H01L 21/308* | (2006.01) |
| *H01L 21/765* | (2006.01) |
| *H01L 21/8234* | (2006.01) |
| *H01L 29/10* | (2006.01) |
| *H01L 29/36* | (2006.01) |
| *H01L 29/40* | (2006.01) |
| *H01L 29/423* | (2006.01) |
| *H01L 29/66* | (2006.01) |
| *H01L 29/739* | (2006.01) |
| *H01L 29/78* | (2006.01) |
| *H10B 63/00* | (2023.01) |

(52) U.S. Cl.
CPC .... *H01L 21/2253* (2013.01); *H01L 21/26513* (2013.01); *H01L 21/26586* (2013.01); *H01L 21/266* (2013.01); *H01L 21/3081* (2013.01); *H01L 21/765* (2013.01); *H01L 21/823487* (2013.01); *H01L 29/0684* (2013.01); *H01L 29/1079* (2013.01); *H01L 29/1095* (2013.01); *H01L 29/36* (2013.01); *H01L 29/407* (2013.01); *H01L 29/4236* (2013.01); *H01L 29/66348* (2013.01); *H01L 29/66734* (2013.01); *H01L 29/66803* (2013.01); *H01L 29/7397* (2013.01); *H01L 29/7813* (2013.01); *H01L 29/7827* (2013.01); *H10B 63/34* (2023.02)

(58) Field of Classification Search
CPC ......... H01L 29/66348; H01L 29/66734; H01L 29/7397; H01L 29/7813; H01L 29/7827; H01L 29/66803; H01L 21/0415; H01L 21/046; H01L 21/2253; H01L 21/26513; H01L 21/266; H01L 21/3081; H01L 21/765; H01L 21/823487; H10B 63/34

See application file for complete search history.

(56) References Cited

U.S. PATENT DOCUMENTS

| | | |
|---|---|---|
| 2005/0179082 A1 | 8/2005 | Miyata et al. |
| 2007/0249123 A1 | 10/2007 | Chou et al. |
| 2010/0285646 A1 | 11/2010 | Lin et al. |
| 2011/0001187 A1 | 1/2011 | Hebert |
| 2012/0261714 A1* | 10/2012 | Taketani ............. H01L 29/7808 257/E29.198 |
| 2013/0313633 A1 | 11/2013 | Shen et al. |
| 2016/0247916 A1* | 8/2016 | Stefanov ............... H01L 27/088 |
| 2017/0194486 A1* | 7/2017 | Venkatraman .... H01L 29/66734 |
| 2018/0226480 A1 | 8/2018 | Okuda et al. |
| 2020/0227537 A1* | 7/2020 | Li ....................... H01L 29/7811 |
| 2021/0111279 A1* | 4/2021 | Ryu .................. H01L 29/66333 |

* cited by examiner

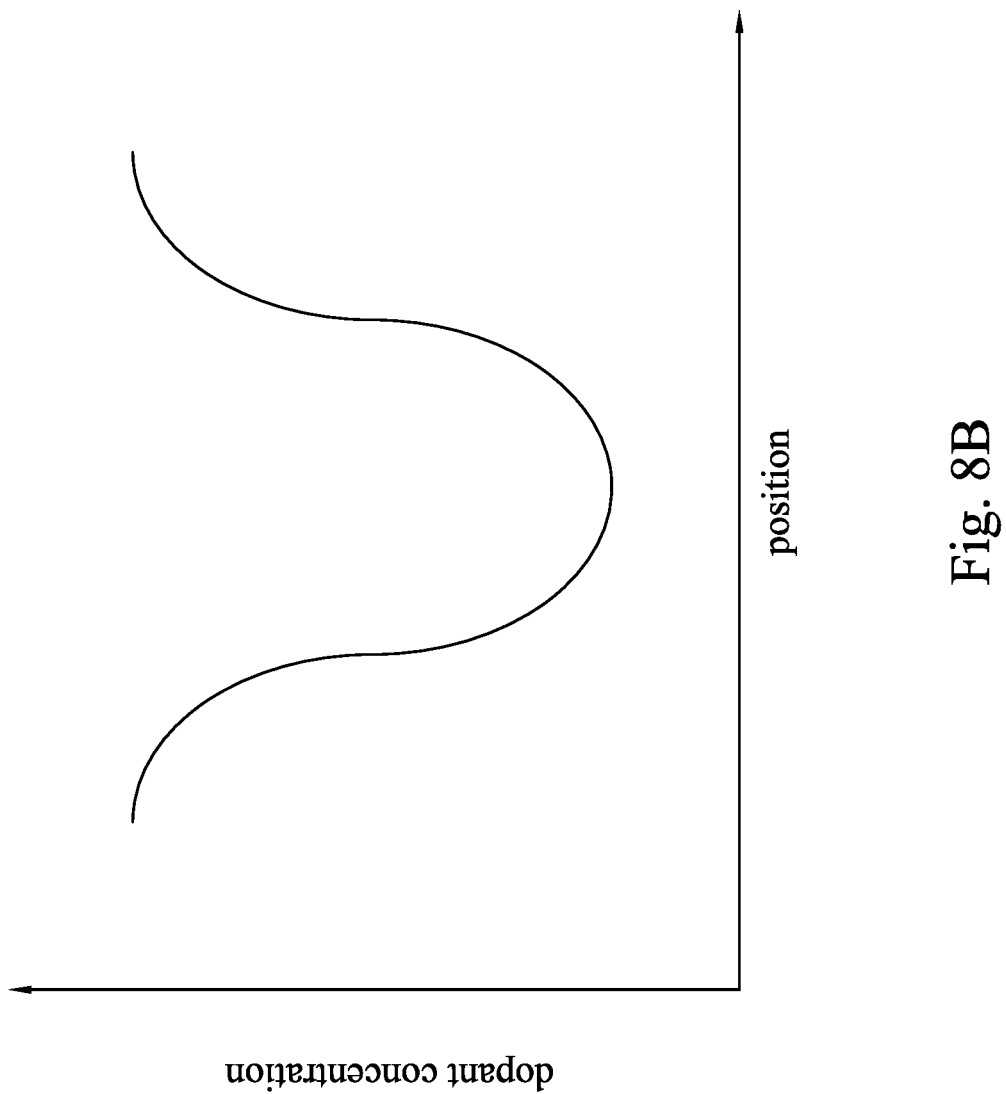

SEMICONDUCTOR DEVICE AND MANUFACTURING METHOD THEREOF

CROSS-REFERENCE TO RELATED APPLICATION

The present application is a Continuation application of U.S. application Ser. No. 17/666,386, filed on Feb. 7, 2022, which is a Divisional application of U.S. application Ser. No. 16/859,840, filed on Apr. 27, 2020, now U.S. Pat. No. 11,244,830, issued on Feb. 8, 2022, which claims priority to China Application Serial No. 202010186664.7, filed on Mar. 17, 2020, which are hereby incorporated herein by references in their entireties.

BACKGROUND

The semiconductor integrated circuit (IC) industry has experienced rapid growth. Technological advances in IC materials and design have produced generations of ICs where each generation has smaller and more complex circuits than the previous generation. Such advances have increased the complexity and challenges of processing and manufacturing of ICs.

Vertically-conducting trench MOSFETs (metal oxide semiconductor field effect transistors) can be used as power electronics. When a trench MOSFET is biased in the on state, current flows vertically between source regions and substrate. Reducing cell pitch of MOSFETs is crucial in reducing the device sizes and in increasing the number of active devices on a semiconductor chip. In addition, cell pitch also affects device performance, such as the resistivity between source and drain when the device is on (Rdson). Reducing cell pitch is limited by the manufacturing process technology, such as the capability of lithographical tool in resolving minimum critical dimension and in aligning different patterning layers. It is within this context the following disclosure arises.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
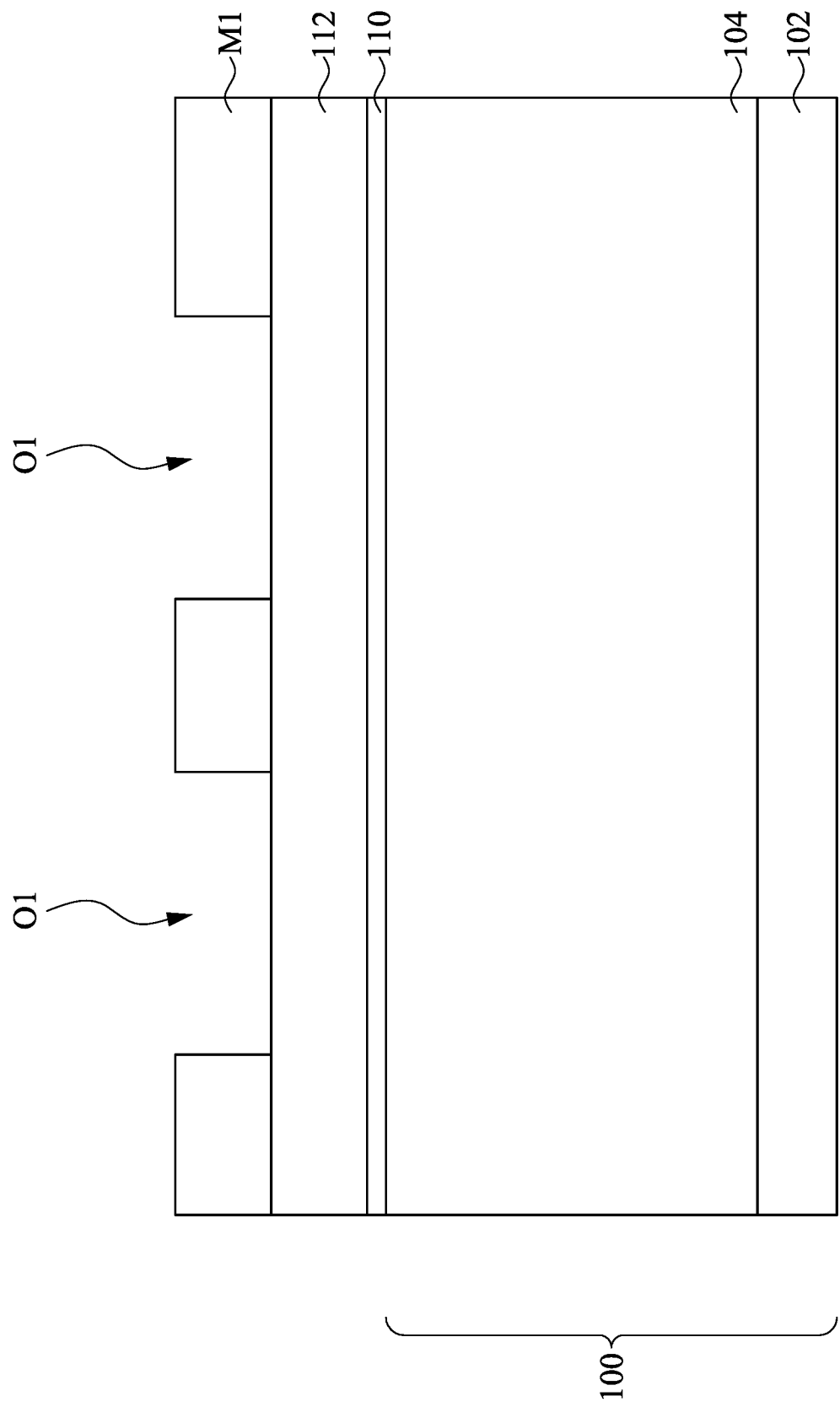
FIGS. 1 to 14 are cross-sectional views of a semiconductor device in various stages of fabrication in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIGS. 1 to 14 are cross-sectional views of a semiconductor device in various stages of fabrication in accordance with some embodiments of the present disclosure.

Reference is made to FIG. 1. Shown there is a semiconductor region 102, which is a portion of a semiconductor substrate 100, is provided. The semiconductor region 102 may have a crystalline silicon structure. Alternatively, semiconductor region 102 may be formed of other semiconductor materials such as silicon germanium. In some embodiments, semiconductor region 102 is a heavily doped layer doped with an n-type impurity such as phosphorous or arsenic, for example, to an impurity concentration between about $10^{19}/cm^3$ and about $10^{21}/cm^3$. In the described embodiments, the term "heavily doped" means an impurity concentration of above about $10^{19}/cm^3$. One skilled in the art will recognize, however, that "heavily doped" is a term of art that depends upon the specific device type, technology generation, minimum feature size, and the like. It is intended, therefore, that the term be interpreted in light of the technology being evaluated and not be limited to the described embodiments.

Over the heavily doped semiconductor region 102, the semiconductor substrate 100 further includes an epitaxy layer 104. The epitaxy layer 104 is formed through epitaxy, and is lightly doped with an n-type impurity. The impurity concentration of epitaxy layer 104 may be between about $10^{15}/cm^3$ and about $10^{18}/cm^3$. As a result, the impurity concentration of the epitaxy layer 104 is lower than the impurity concentration of the semiconductor region 102. In some embodiments, the epitaxy layer 104 may be a crystalline silicon layer, although other semiconductor material may be used.

A pad oxide layer 110 and a hard mask 112 are then formed over the epitaxy layer 104. In some embodiments, the pad oxide layer 110 is formed by thermally oxidizing a top region of the epitaxy layer 104, and hence the pad oxide layer 110 may include silicon oxide ($SiO_2$). The hard mask 112 may be formed of silicon nitride, such as $Si_3N_4$, and may be formed by suitable process, such as CVD, PVD, ALD, or other suitable processes.

A patterned mask M1 is then formed on the hard mask 112. In some embodiments, the patterned mask M1 has a plurality of openings O1, which define the positions of the gate structures formed in later steps (e.g., the gate structures 170 in FIGS. 10-14). In some embodiments, the patterned mask M1 is photoresist, and may be formed by photolithography process.

Figure 2:
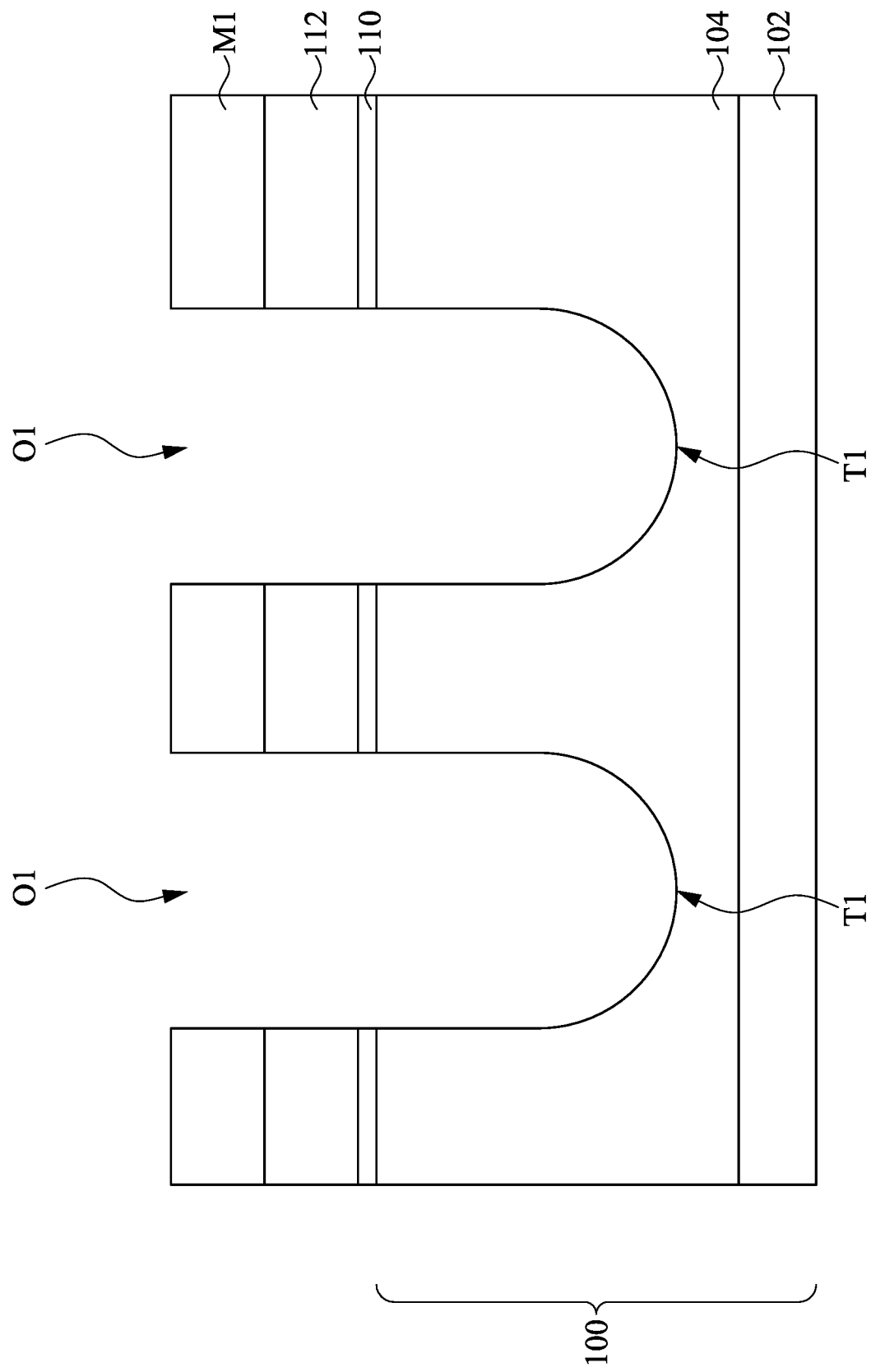

Reference is made to FIG. 2. The pad oxide layer 110, the hard mask 112, and the epitaxy layer 104 are etched via the openings O1 of the patterned mask M1, so as to form a plurality of trenches T1 in the epitaxy layer 104. In greater detail, the hard mask 112 is patterned using the patterned mask M1 as an etching mask. Then, the pad oxide layer 110 and the epitaxy layer 104 are patterned using the hard mask 112 as an etching mask. In some embodiments, the pad oxide layer 110, the hard mask 112, and the epitaxy layer 104 may be etched using dry etching, wet etching, or combinations thereof. In some embodiments, each of the trenches T1 has a rounded bottom surface. Alternatively, the each of the trenches T1 has a U-shaped cross-sectional profile. In some embodiments, the bottommost ends of the trenches T1 are separated from the semiconductor region 102.

Figure 3:
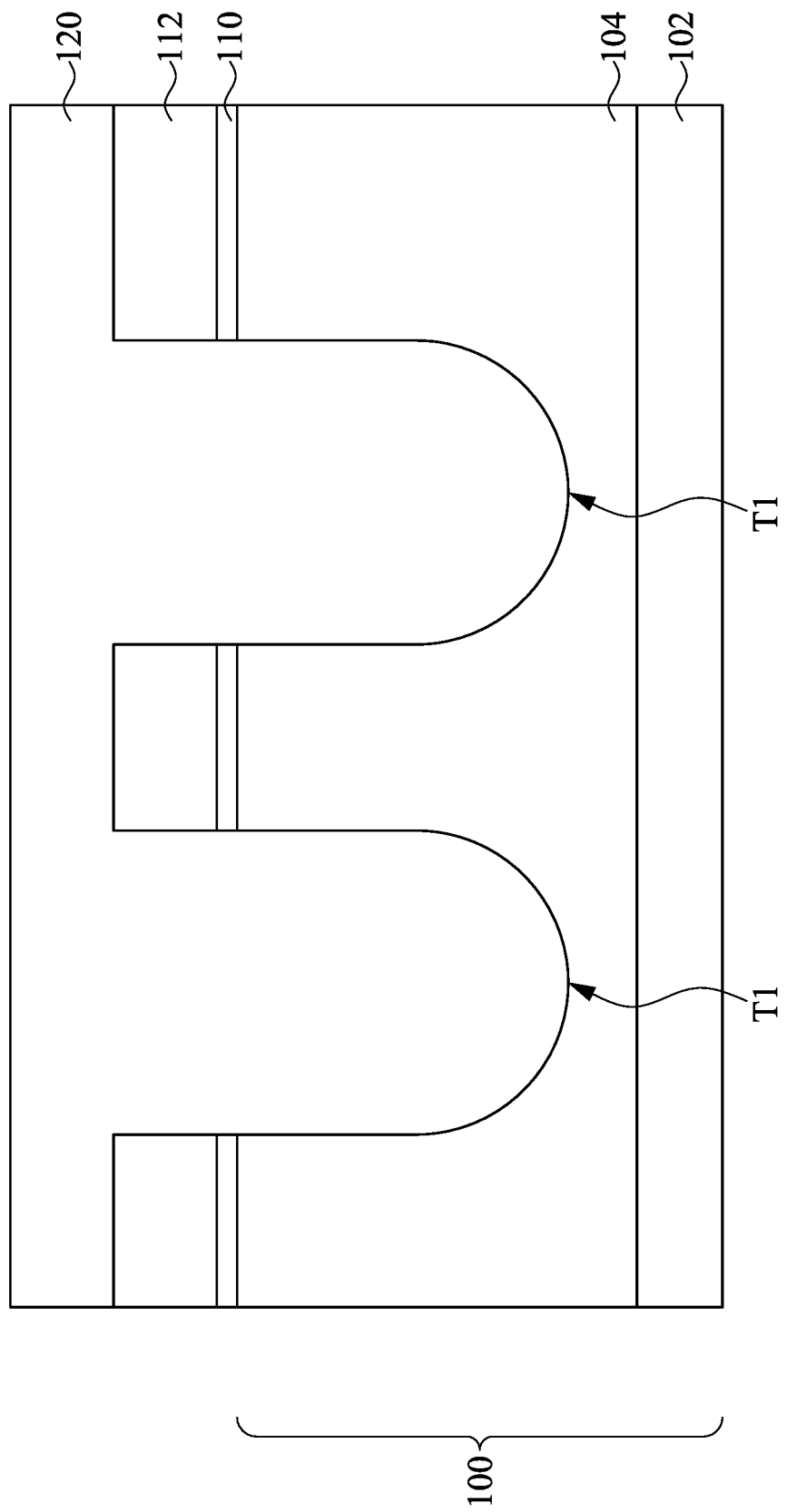

Reference is made to FIG. 3. The patterned mask M1 is removed by suitable process, such as stripping. Then, an oxide layer 120 is deposited over the hard mask 112 and fills the trenches T1. In some embodiments, the oxide layer 120 completely fills the trenches T1. That is, no portion of the trenches T1 is unfilled by the oxide layer 120. In some embodiments, the oxide layer 120 is made of $SiO_2$. In some embodiments, the oxide layer 120 may be formed by CVD, PVD, ALD, flowable CVD, or other suitable deposition processes.

Figure 4:
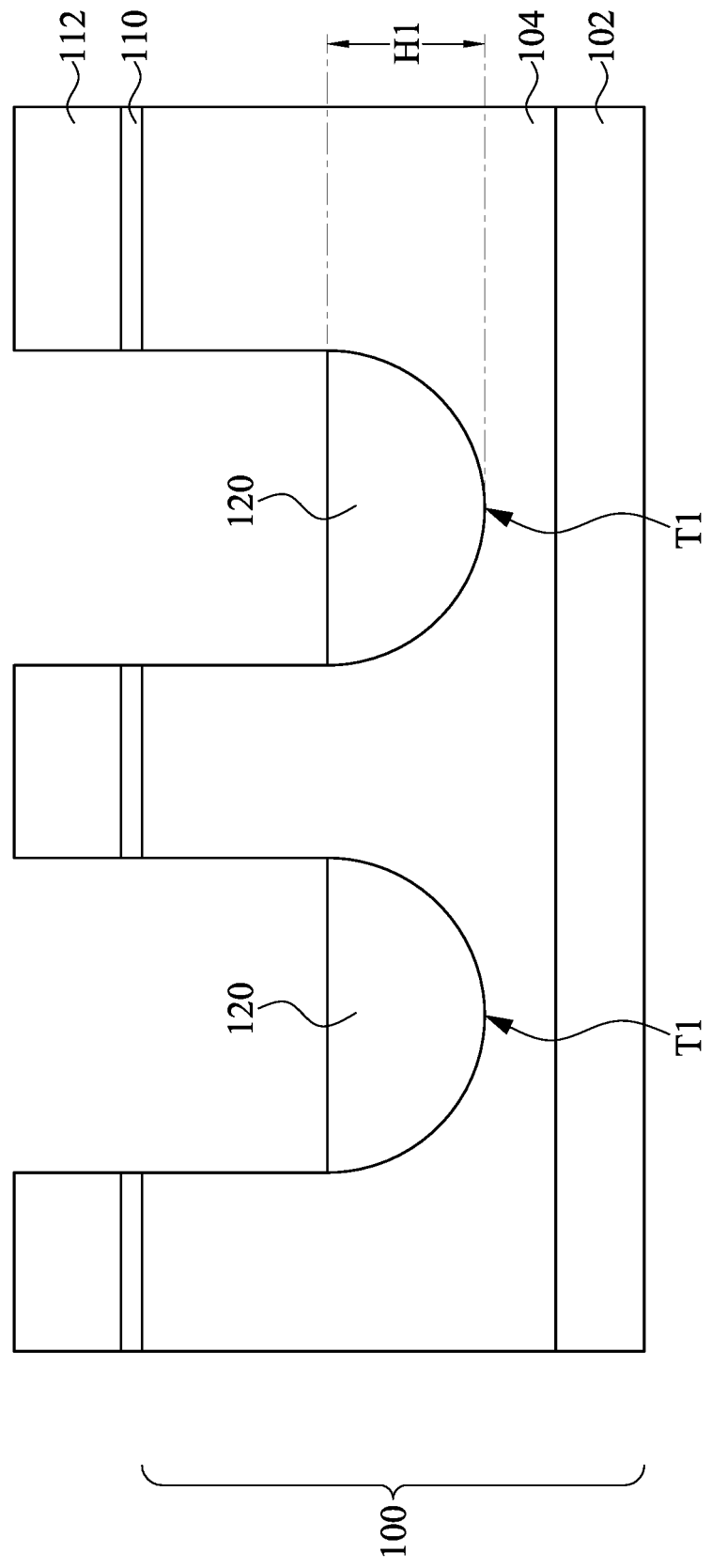

Reference is made to FIG. 4. The oxide layer 120 is etched back, so as to lower the top surface of the oxide layer 120. The remaining oxide layer 120 retains in the lower portions of the trenches T1. For example, the oxide layer 120 is lowered such that the topmost surface of the remaining oxide layer 120 is lower than the topmost surface of the epitaxy layer 104. Stated another way, the remaining portions of the oxide layer 120 is disposed in a bottom portion of the trenches T1. The oxide layer 120 may be etched using dry etching, wet etching, or combinations thereof. In some other embodiments, a chemical mechanism polishing (CMP) process to the oxide layer 120 to level the top surface of the oxide layer 120 and the top surfaces of the hard mask 112 is performed prior to etching back the oxide layer 120. In some embodiments, after the etching back process, the oxide layer 120 has a greatest height H1 in a range from about 0.5 μm to about 3.5 μm.

Figure 5A:
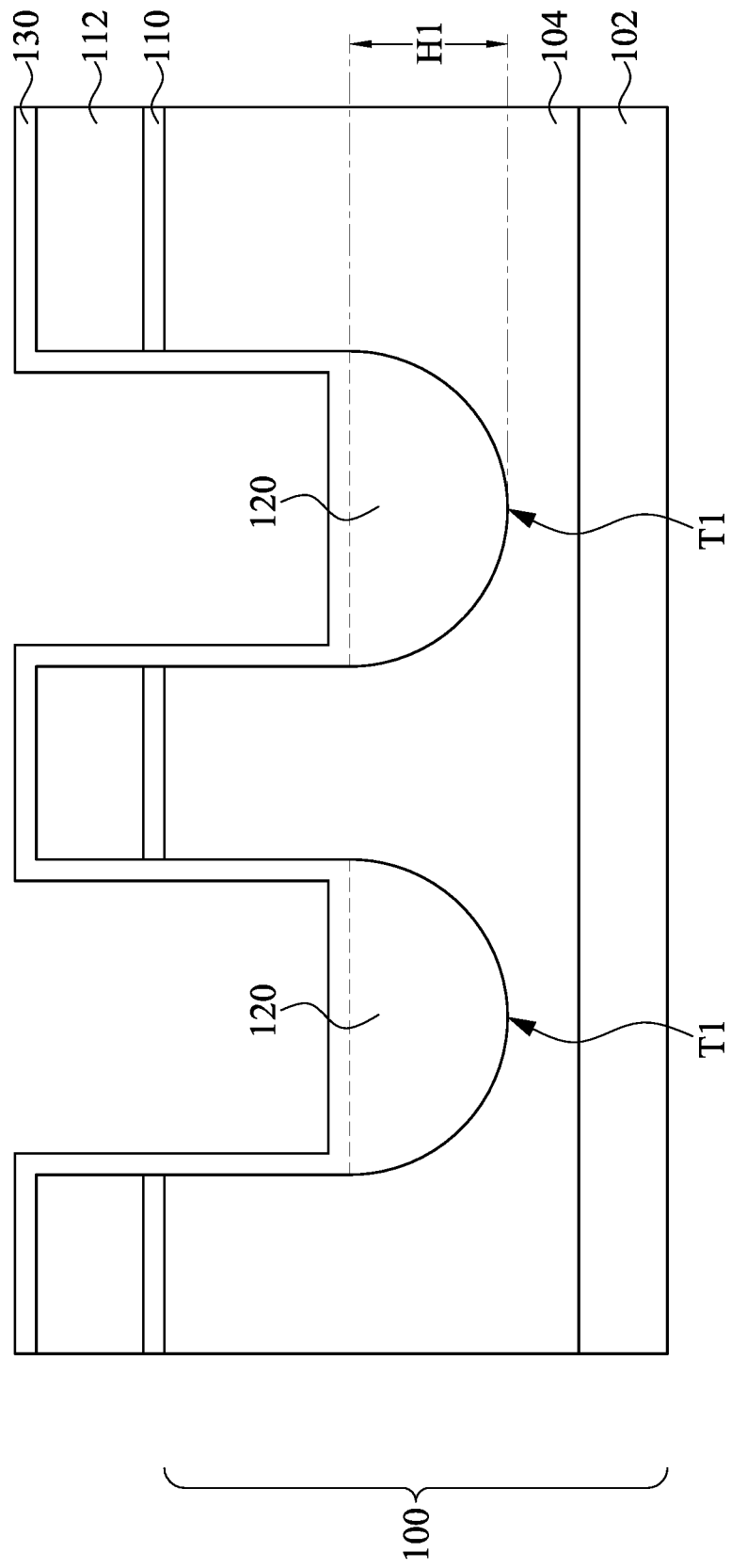

Reference is made to FIG. 5A. An oxide layer 130 is deposited over the hard mask 112 and on the sidewalls of the trenches T1. In some embodiments, the oxide layer 130 is conformal to the hard mask 112, the pad oxide layer 110, and the epitaxy layer 104. As a result, the oxide layer 130 is formed by a conformal deposition process, such as CVD or ALD, at a time duration short enough to form a conformal layer without filling the trenches T1. In some embodiments where the oxide layer 120 and the oxide layer 130 are both formed by CVD, the deposition time of the oxide layer 120 may be longer than the deposition time of the oxide layer 130, because the oxide layer 120 is deposited to completely fill the trenches T1 (see FIG. 3), while the oxide layer 130 is a thin layer conformal to the underlying structures. As a result, the thickness of the oxide layer 120 in FIG. 3 is thicker than the oxide layer 130 in FIG. 5A. In some embodiments, the oxide layer 130 is made of $SiO_2$. In some embodiments of FIG. 5A, the oxide layers 120 and 130 are made of the same material, and thus there is no distinguishable interface between the oxide layers 120 and 130. While in some embodiments where the oxide layers 120 and 130 are made of different materials, the oxide layers 120 and 130 may include a distinguishable interface therebetween.

Figure 5B:
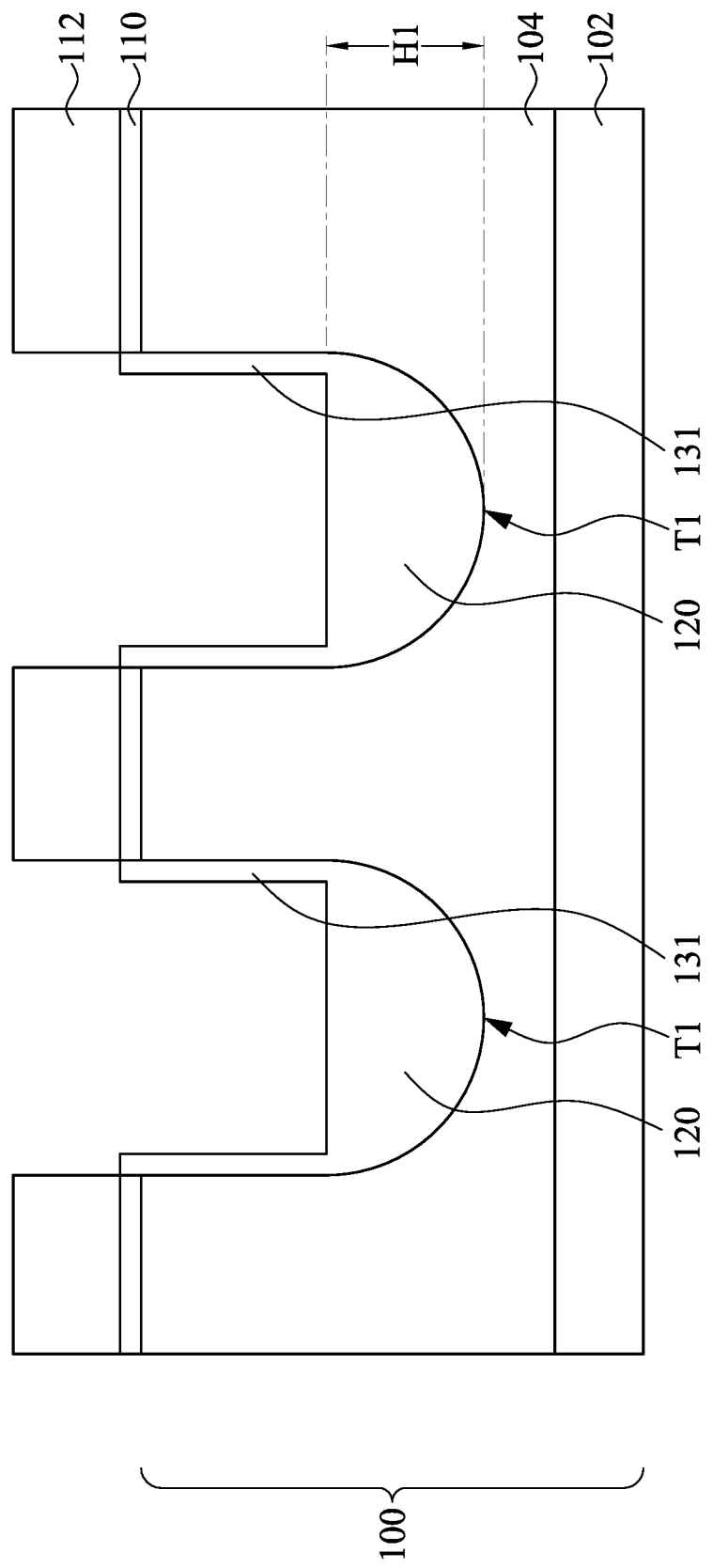

Reference is made to FIG. 5B. FIG. 5B illustrates other embodiments different from the embodiments of FIG. 5A, in that an oxide layer 131 is selectively formed on the surfaces of the epitaxy layer 104 exposed by the trenches T1. In some embodiments, the oxide layer 131 may be formed via a thermal oxidation process. In this way, the oxide layer 131 may have a faster growing rate on the exposed surfaces of the epitaxy layer 104 than on the hard mask 112. In some embodiments, the surfaces of the hard mask 112 are free from coverage by the oxide layer 131. That is, the surfaces of the hard mask 112 are kept exposed after forming the oxide layer 131.

Figure 6A:
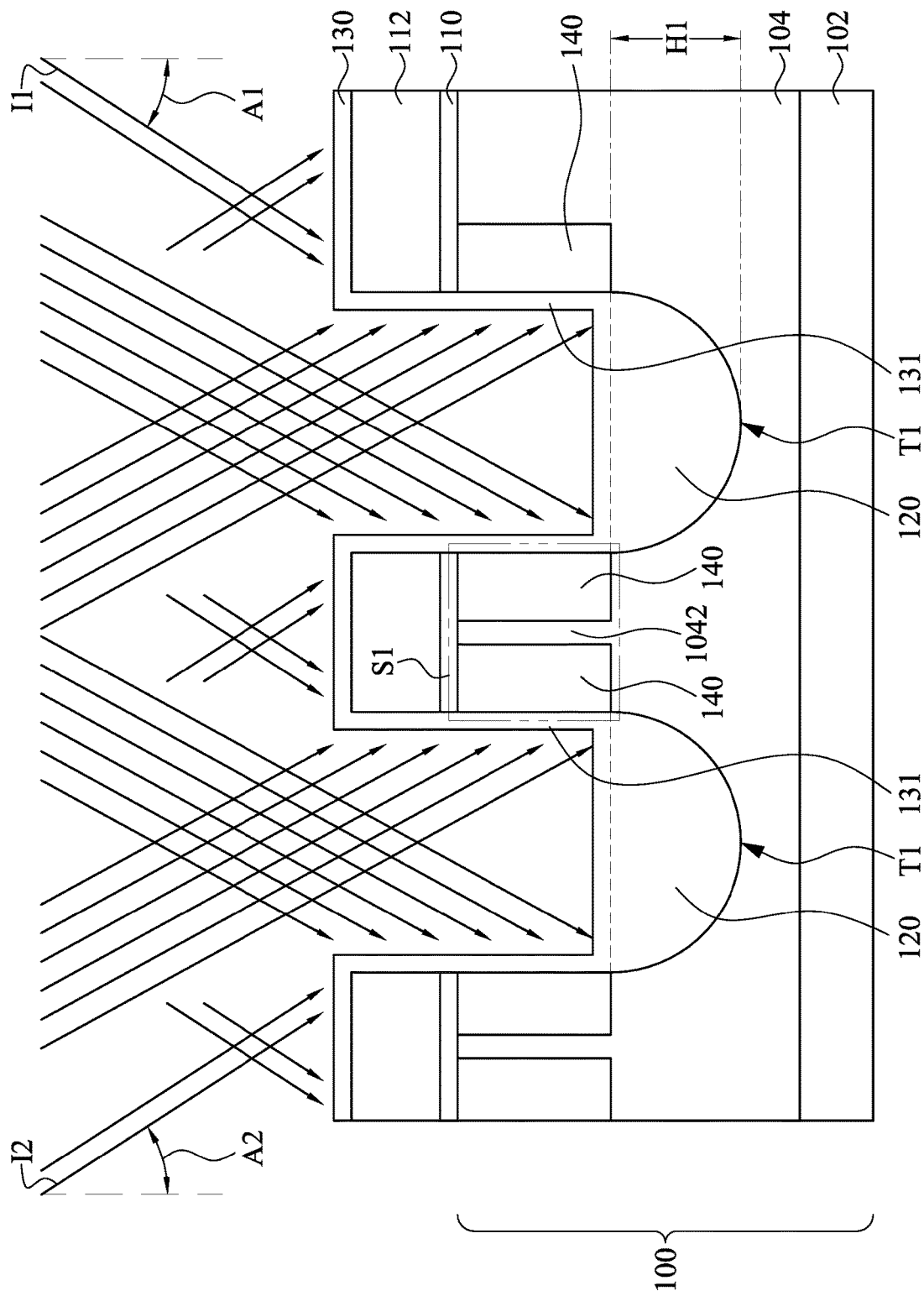
Figure 6B:
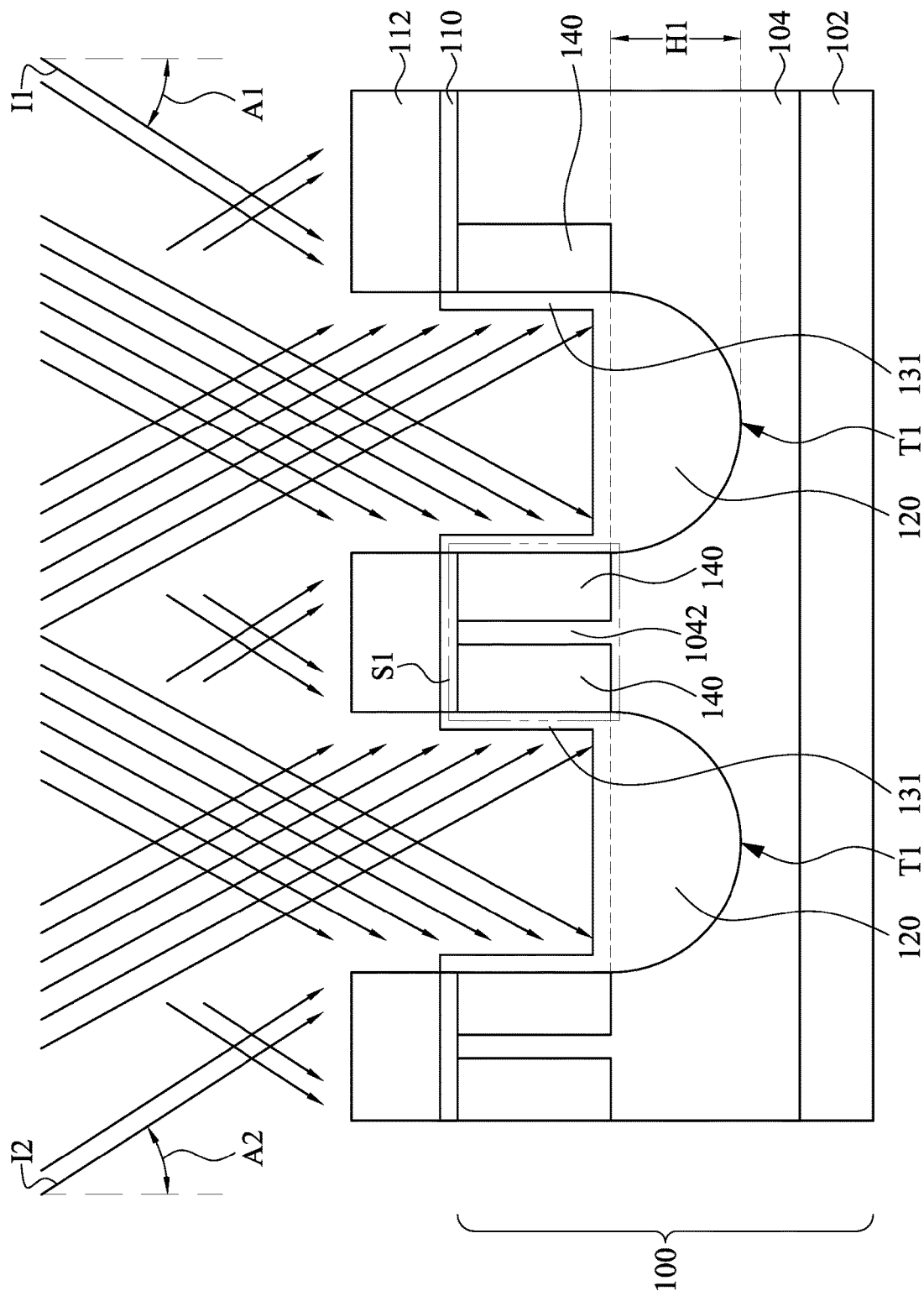

Reference is made to FIGS. 6A and 6B, in which FIG. 6A follows the embodiments of FIG. 5A, and FIG. 6B follows the embodiments of FIG. 5B. A directional implantation process is performed to form a plurality of P-well regions 140 in the epitaxy layer 104, in which directional ions are directed to the epitaxy layer 104 at oblique angles with respect to a perpendicular to the topmost surface of the epitaxy layer 104. The arrows with dashed lines in FIGS. 6A and 6B indicate the ion beams that are incident to the epitaxy layer 104. In greater detail, the ion beams are directed to the epitaxy layer 104 from the sidewalls of the epitaxy layer 104 via the trenches T1, while the hard mask 112 blocks the incident ion beams such that the ion beams cannot reach the top surfaces of the epitaxy layer 104.

In some embodiments, the directional implantation process can be performed by, for example, directing first directional ions I1 to the epitaxy layer 104 via a first side of the trenches T1 (e.g., left side of the trenches T1 in FIGS. 6A and 6B) at a first angle A1 ranged from about 30° to about 60°, so as to form portions of the P-well regions 140 in the epitaxy layer 104 via the first side of the trenches T1. Here, the angle A1 indicates the angle between the incident direction of the first directional ions I1 and the normal line of the topmost surface of the epitaxy layer 104. After directing the first directional ions I1, second directional ions I2 are directed to epitaxy layer 104 via a second side of the trenches T1 (e.g., right side of the trenches T1 in FIGS. 6A and 6B) that is opposite to the first side of the trenches T1 at a second angle A2 ranged from about 30° to about 60°, so as to form other portions of the P-well regions 140 in the epitaxy layer 104 via the second side of the trenches T1. Here, the angle A2 indicates the angle between the incident direction of the second directional ions I2 and the normal line of the topmost surface of the epitaxy layer 104. In some embodiments, the first deposition angle A1 and the second deposition angle A2 have substantially the same value but with opposite directions. In some embodiments, if the first and second angles A1, A2 are too small (e.g., much lower than 30°), the ions' trajectories may be too steep and thus are unable to reach a desired lateral depth in the epitaxy layer 104. On the other hand, if the first and second angles A1, A2 are too large (e.g., much greater than 60°), the ions' trajectories may be too horizontal and thus are blocked by the hard mask 112.

In some embodiments, after the directional implantation process, the epitaxy layer 104 has an un-doped region 1042 laterally adjacent to the P-well regions 140. That is because the directional ions I1 and I2 are unable to reach the un-doped region 1042 from the sidewalls of the epitaxy layer 104. For example, as shown in a region S1 in FIGS. 6A and 6B (drawn in dash-line), in which region S1 is the region of epitaxy layer 104 between two adjacent trenches T1

(and/or the region between two adjacent gate structures in FIGS. 10-14). As illustrated, an un-doped region 1042 is laterally formed between two P-well regions 140. In some embodiments, the topmost end of the un-doped region 1042 is substantially level with the topmost surface of the epitaxy layer 104. Stated another way, the topmost surface of the region S1 of the epitaxy layer 104 at least in part is un-doped after the directional implantation process. In some embodiments, the region S1 has higher dopant concentrations on its opposite sides than its middle. For example, the middle of the region S1 (e.g., the un-doped region 1042) is free of dopants of the P-well regions 140.

In some embodiments, the oxide layers 130 and 131 of FIGS. 6A and 6B act as protective layers (e.g., screening layers) of the epitaxy layer 104 during the direction implantation process for implantation screening and reduction of the channeling effect during the directional implantation process. In some embodiments where the oxide layers 130 and 131 of FIGS. 6A and 6B are absent, the sidewalls of the epitaxy layer 104 may be exposed by the trenches T1, and thus the ions I1 and I2 may directly attack the exposed sidewalls of the epitaxy layer 104 and may cause defects in the epitaxy layer 104. Accordingly, the oxide layers 130 and 131 of FIGS. 6A and 6B can protect the epitaxy layer 104 by suppressing the defects in the epitaxy layer 104 caused by the directional implantation process described herein.

In some embodiment, the oxide layer 120 can also act as a mask to block the ions I1 and I2, so as to prevent the ions I1 and I2 from going to unwanted regions of the epitaxy layer 104, and thus the height H1 of the oxide layer 120 affects the vertical depth of the P-well regions 140. As mentioned above, the oxide layer 120 has a height H1 in a range from about 0.5 µm to about 3.5 µm. In some embodiments, if the height H1 of the oxide layer 120 is too low, the P-well regions 140 may be too long along the vertical direction; if the height H1 of the oxide layer 120 is too large, the P-well regions 140 may be too short along the vertical direction.

In some embodiments of the present disclosure, the hard mask 112 is used for patterning the epitaxy layer 104 to form trenches T1 in the epitaxy layer 104. Then, the P-well regions 140 can be formed, using the same hard mask 112, in the epitaxy layer 104 by performing a directional implantation process. In some embodiments, all of the P-well regions 140 are formed in the regions underlying the hard mask 112, and thus the P-well regions 140 can be regarded as substantially self-aligned with the hard mask 112. However, in some embodiments where P-well regions are formed in later steps (e.g., after the hard mask 112 is removed), an additional mask may be applied to define positions of P-well regions in the epitaxy layer 104. Accordingly, embodiments of the present disclosure provide a method to form self-aligned P-well regions, and can also save cost.

Figure 7:
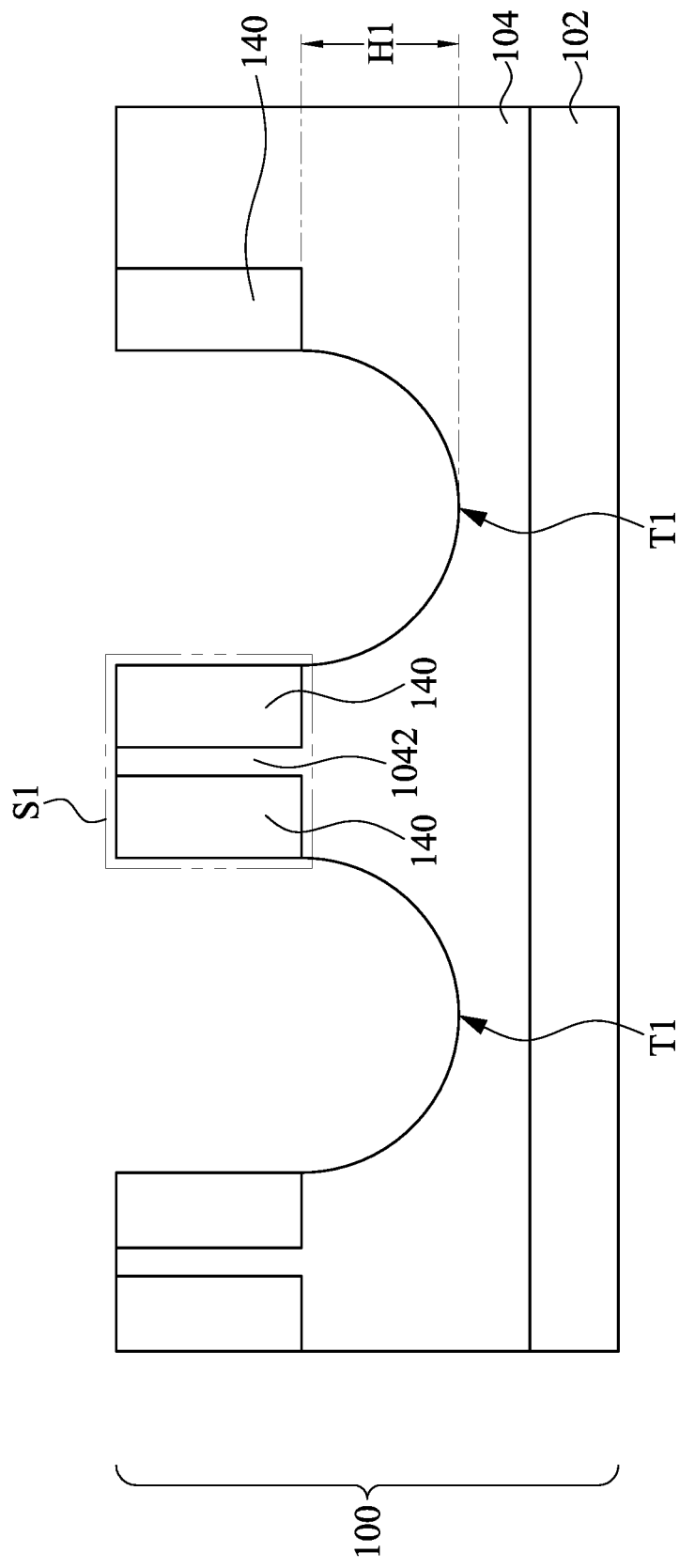

Reference is made to FIG. 7. The hard mask 112, the pad oxide 110, the oxide layer 120, and the oxide layer 130 in FIG. 6A (and also the oxide layer 131 in FIG. 6B) are removed. In some embodiments, the hard mask 112, the pad oxide layer 110, the oxide layer 120, and the oxide layer 130 (or oxide layer 131) can be removed via suitable etching process, such as dry etching, wet etching, or combinations thereof. After the etching process, the topmost surfaces of the epitaxy layer 104 are exposed. In some embodiments, the un-doped regions 1042 are exposed after the etching process.

Figure 8A:
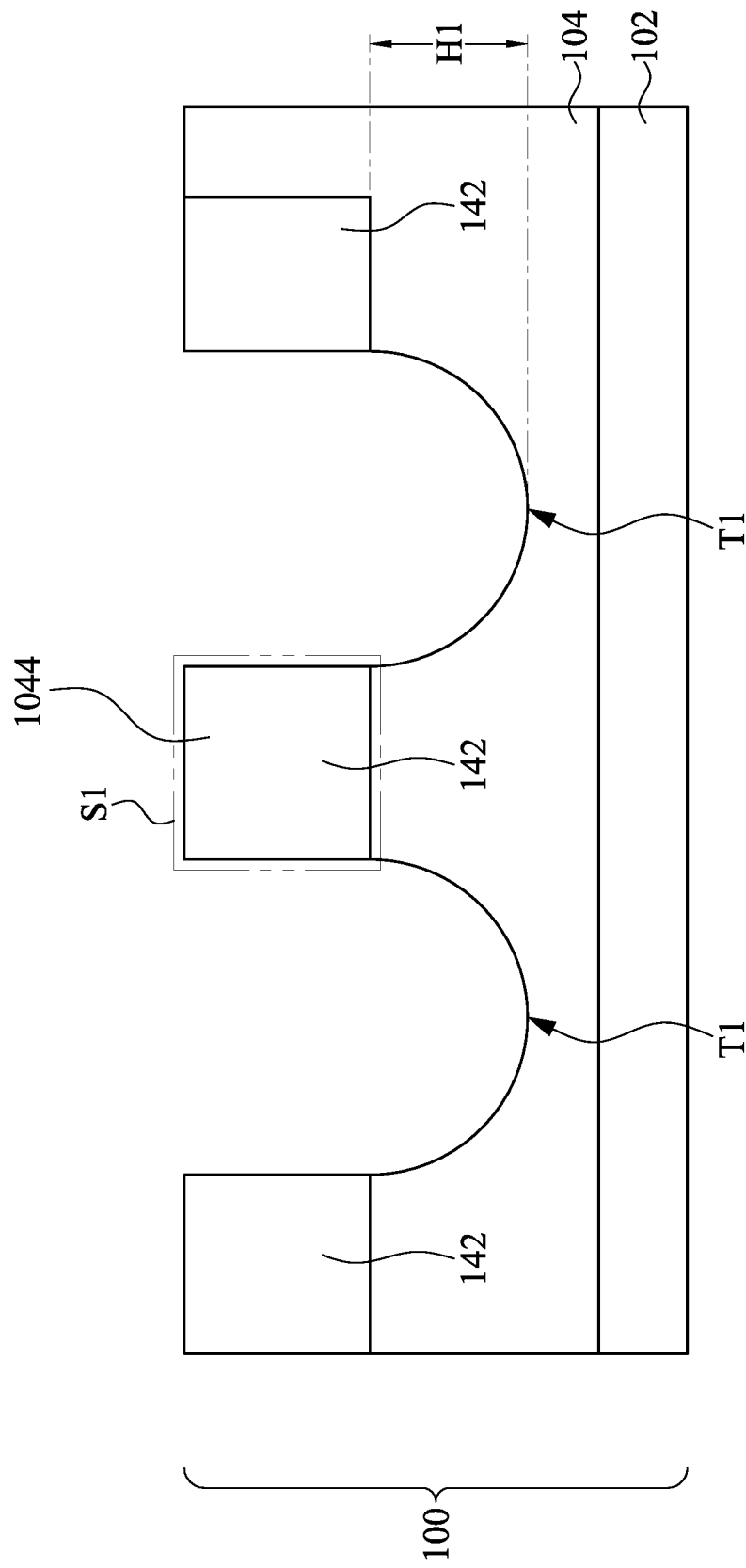

Reference is made to FIG. 8A. An annealing process is performed to redistribute the P-well regions 140 of FIG. 7 to form P-well regions 142. In greater detail, the annealing process is performed to laterally diffuse the dopants of the P-well regions 140 of FIG. 7. For example, as shown in region S1 between two adjacent trenches T1, the dopants of P-well regions 140 of FIG. 7 are diffused to the un-doped region 1042 of FIG. 7 via thermodynamic, such that the un-doped region 1042 becomes a doped region 1044, as shown in FIG. 8A. Stated another way, the topmost surface of the epitaxy layer 104 in region S1 is a fully doped region after the annealing process. In some embodiments, the annealing process may be performed under a temperature between about 800° C. to about 1200° C. for about 30 minutes to about 240 minutes.

Reference is made to FIG. 8B, in which FIG. 8B is graph illustrating a dopant concentration distribution in region S1 of FIG. 8A. The vertical axis of FIG. 8B is the dopant concentration and the horizontal axis of FIG. 8B is the lateral position of region S1 in FIG. 8A (e.g., from the left trench T1 to the right trench T1). As shown in FIG. 8B, the dopant concentration laterally varies in the region S1. In greater detail, the region S1 has higher dopant concentrations at its opposite sides, which are close to the trenches T1 in FIG. 8A. This is because the dopants are driven into the region S1 initially from the opposite sides of the region S1, as described in FIGS. 6A and 6B. On the other hand, because the annealing process diffuses the dopants from the opposite sides of the region S1 to the middle of the region S1, the dopant concentration at the middle of the region S1 is lower than the dopant concentrations at the opposite sides of the region S1. The characteristic can be found at the topmost surface of the region S1. That is, the dopant concentration varies along the topmost surface of the region S1 of the epitaxy layer 104.

Figure 9:
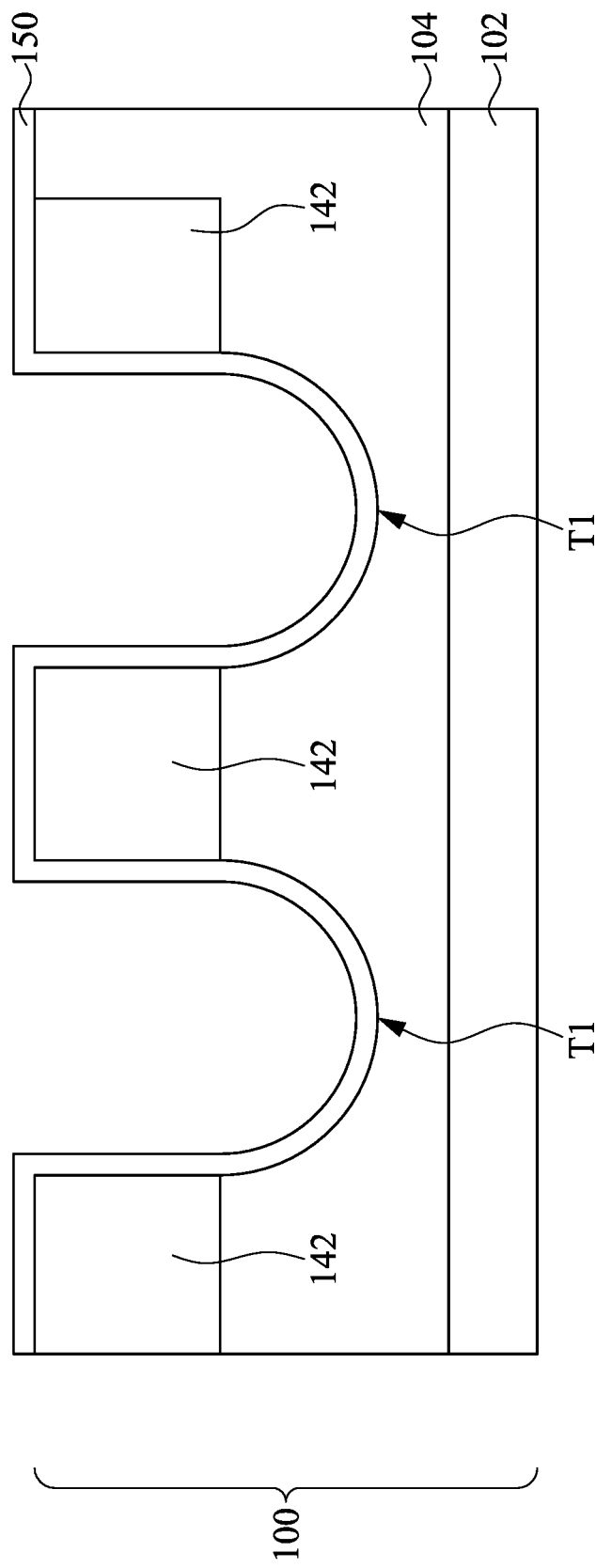

Reference is made to FIG. 9. A gate dielectric layer 150 is deposited conformal to the epitaxy layer 104. The gate dielectric layer 150 lines the trenches T1. The gate dielectric layer 150 may be oxide layer, such as silicon oxide, silicon dioxide ($SiO_2$). In some embodiments, the gate dielectric layer 150 may be formed by suitable process, such as CVD, ALD, or thermal oxidation process. In some embodiments where the gate dielectric layer 150 is formed by thermal oxidation process, the temperature during the thermal oxidation process may be high enough to cause diffusion of the P-well regions 140 shown in FIGS. 6A and 6B, and may cause a redistribution of the dopants in the P-well regions 140 to form P-well regions 142, as described in FIGS. 8A and 8B. In this way, in some embodiments, the annealing process described in FIGS. 8A and 8B may be skipped as long as the temperature of the thermal oxidation process of FIG. 9 is high enough to cause dopant redistribution. In this situation (e.g., the annealing process discussed in FIGS. 8A and 8B is skipped), the region S1 in FIG. 9 may still have similar dopant concentration distribution as discussed in FIG. 8B, since the temperature of the thermal oxidation process of FIG. 9 is high enough to cause dopant redistribution.

Figure 10:
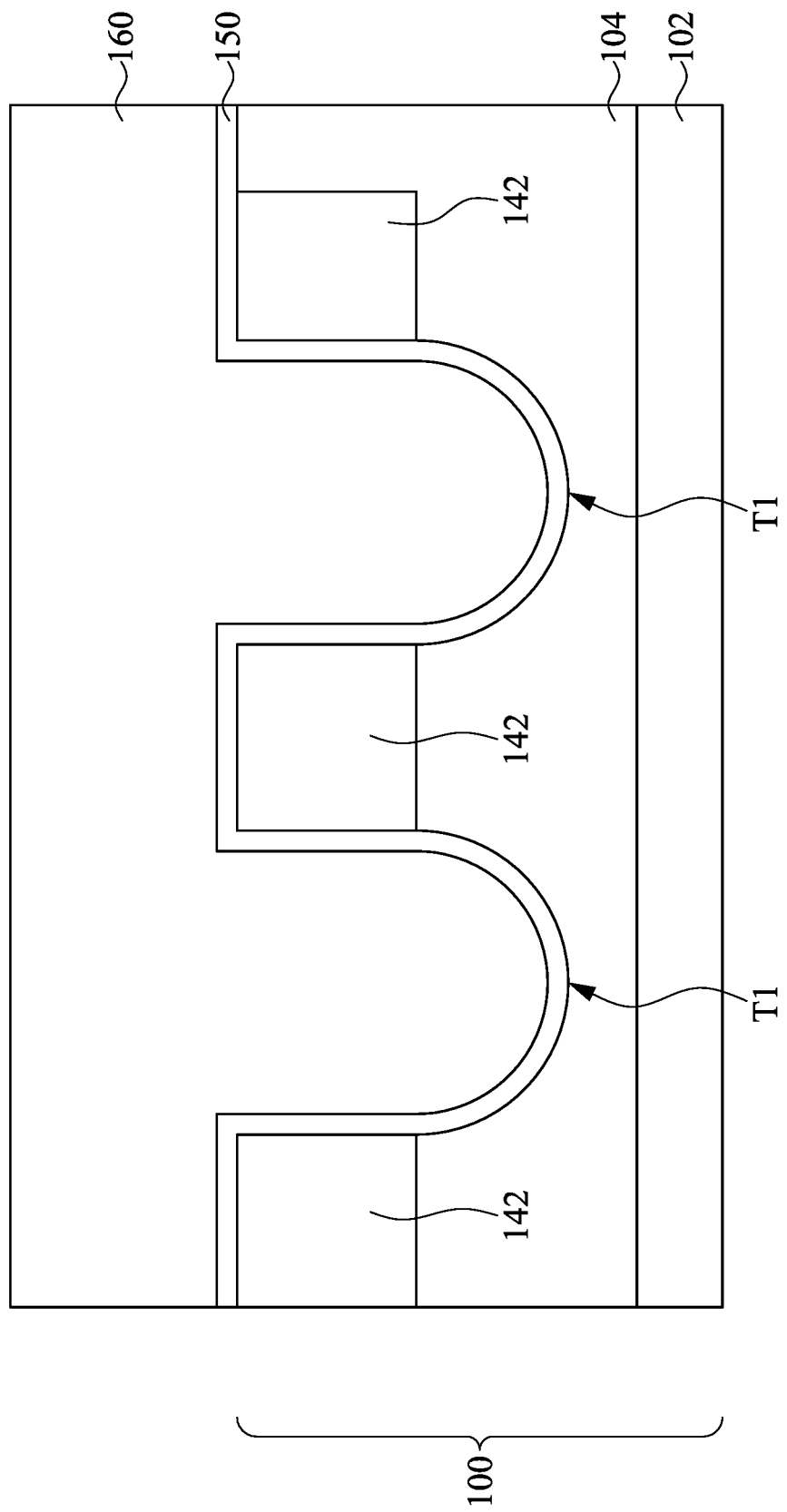

Reference is made to FIG. 10. A gate electrode layer 160 is deposited over the gate dielectric layer 150 and fills the trenches T1. In some embodiments, the gate electrode layer 160 may be polysilicon. In some embodiments, the gate electrode layer 160 may be doped polysilicon. In some embodiments, the gate electrode layer 160 is formed by thermally decomposing silane ($SiH_4$) inside a low-pressure processing chamber. The gate electrode layer 160 is formed to a thickness that fills the trenches T1.

Figure 11:
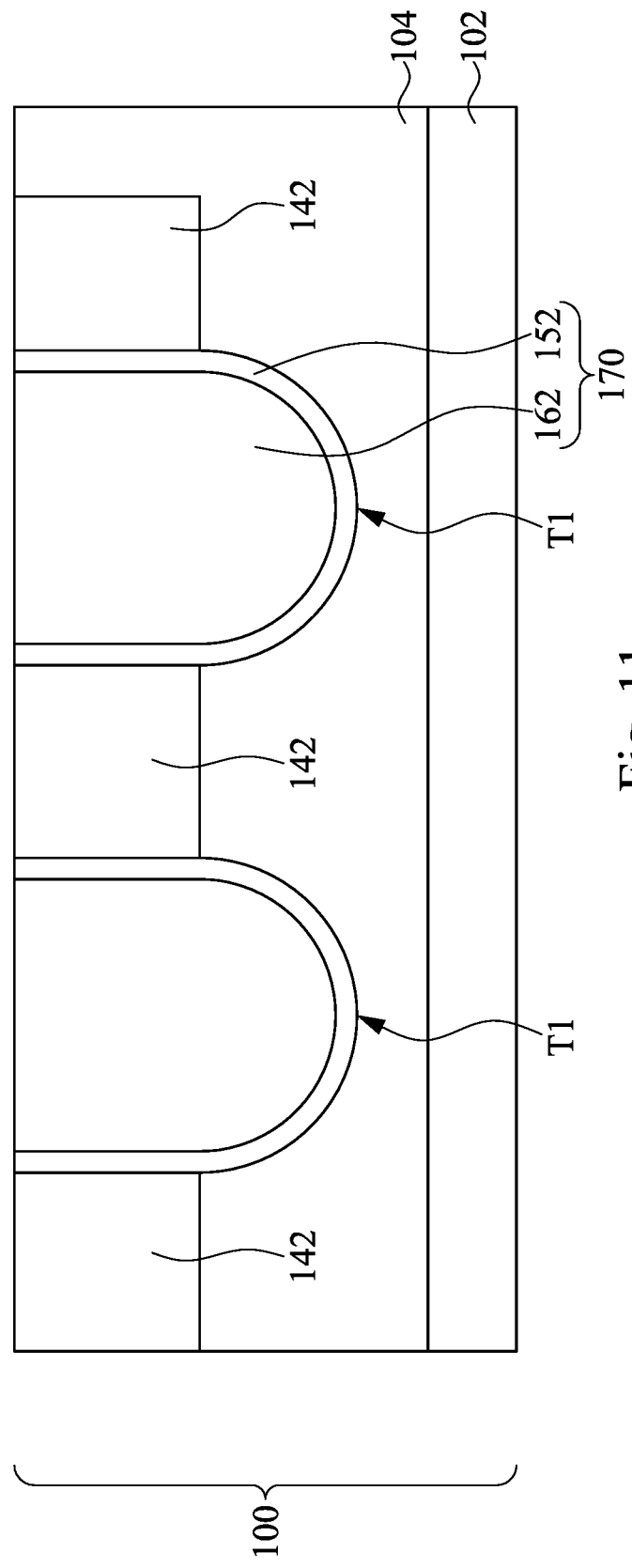

Reference is made to FIG. 11. A chemical mechanism polishing (CMP) process is performed to remove excessive gate electrode layer 160 (see FIG. 10) and the gate dielectric layer 150 until the epitaxy layer 104 is exposed. After the CMP process, the remaining portions of the gate electrode layer 160 in the trenches T1 can be referred to as gate electrodes 162, and the remaining portions of the gate dielectric layer 150 in the trenches T1 can be referred to as gate dielectrics 152. In some embodiments, within each trench T1, the gate electrode 162 and the gate dielectric 152 can be collectively referred to as gate structure 170.

Figure 12:
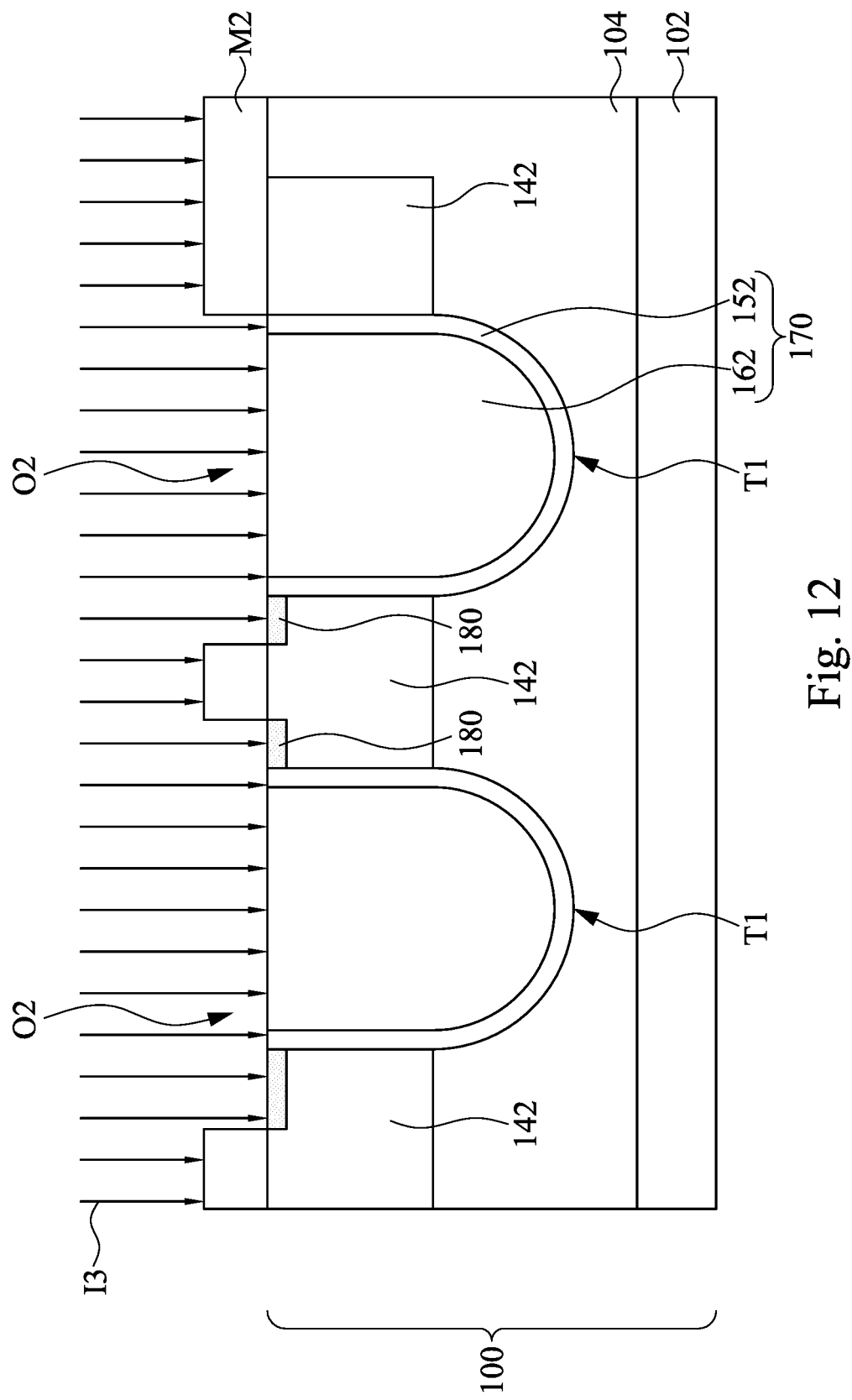

Reference is made to FIG. 12. A patterned mask M2 is formed over the epitaxy layer 104. In some embodiments, the patterned mask M2 has openings O2 to expose the top surfaces of the gate structures 170 and portions of the epitaxy layer 104 adjacent to the gate structures 170. On the other hand, portions of the epitaxy layer 104 are covered by the patterned mask M2. Then, an implantation process is performed to form a plurality of N+ source regions 180 in the exposed portions of the epitaxy layer 104 via the openings O2. The N+ source regions 180 can be referred to as heavily doped N+ regions 180.

In some embodiments, the implantation process of FIG. 12 includes directing ions 13 to the epitaxy layer 104. In some embodiments, the incident direction of the ions 13 is substantially vertical to the top surface of the epitaxy layer 104. That is, the incident direction of the ions 13 is substantially aligned with the normal line of the top surface of the epitaxy layer 104. In some other embodiments, the angle between the incident direction of the ions 13 and the normal line of the top surface of the epitaxy layer 104 ranges from about 0° to about 7°. In the depicted embodiments, at least topmost portions of the gate structures 170 may be unintentionally doped by the ions 13, because the gate structures 170 are not covered by the patterned mask M2. In some other embodiments, the gate structures 170 are covered by the patterned mask M2, so that the gate structures 170 will not be doped by the ions 13.

As discussed above with respect to FIGS. 6A and 6B, the directional ions I1 and I2 are incident to the epitaxy layer 104 at oblique angles. In some embodiments, the incident direction of ions 13 of FIG. 12 are more vertical to the top surface of the epitaxy layer 104 than the incident direction of the ions I1 and I2 described in FIGS. 6A and 6B. Stated another way, the angle between the incident direction of the ions 13 of FIG. 12 and the normal line of the top surface of the epitaxy layer 104 is smaller than the angles between the incident direction of the directional ions I1 and I2 of FIGS. 6A and 6B and the normal line of the top surface of the epitaxy layer 104.

Figure 13:
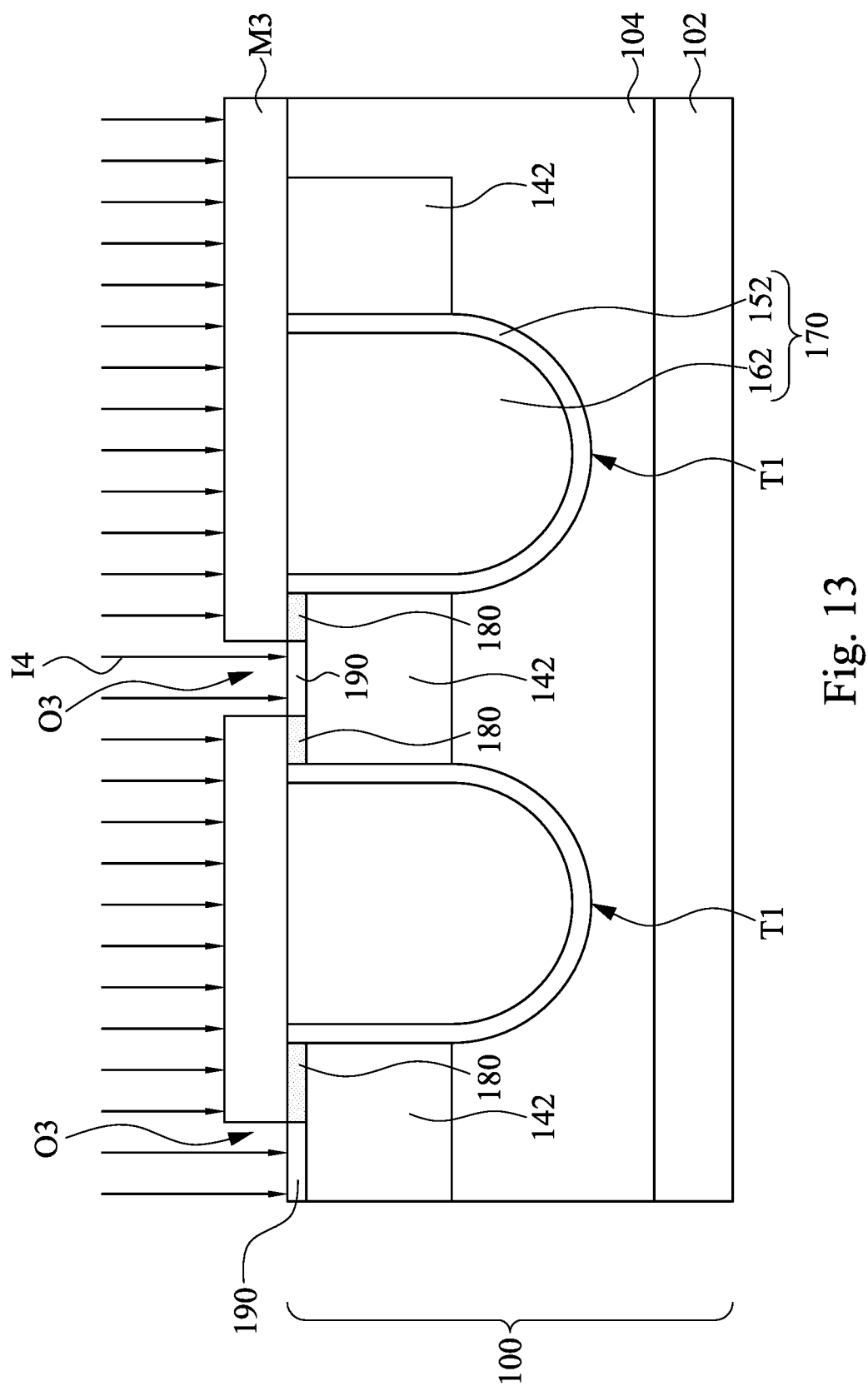

Reference is made to FIG. 13. The patterned mask M2 is removed, and a patterned mask M3 is formed over the epitaxy layer 104. In some embodiments, the patterned mask M3 has openings O3 expose portions of the epitaxy layer 104. On the other hand, the N+ source regions 180 and the gate structures 170 are covered by the patterned mask M3. Then, an implantation process is performed to form a plurality of P+ body regions in the exposed portions of the epitaxy layer 104 via the openings O3. In some embodiments, the dopant concentration in the P+ body regions 190 is higher than the dopant concentration in the P-well region 142.

In some embodiments, the implantation process of FIG. 13 includes directing ions 14 to the epitaxy layer 104. In some embodiments, the incident direction of the ions 14 is substantially vertical to the top surface of the epitaxy layer 104. That is, the incident direction of the ions 14 is substantially aligned with the normal line of the top surface of the epitaxy layer 104. In some other embodiments, the angle between the incident direction of the ions 14 and the normal line of the top surface of the epitaxy layer 104 ranges from about 0° to about 7°.

As discussed above with respect to FIGS. 6A and 6B, the directional ions I1 and I2 are incident to the epitaxy layer 104 at oblique angles. In some embodiments, the incident direction of ions 14 of FIG. 13 are more vertical to the top surface of the epitaxy layer 104 than the incident direction of the ions I1 and I2 described in FIGS. 6A and 6B. Stated another way, the angle between the incident direction of the ions 14 of FIG. 13 and the normal line of the top surface of the epitaxy layer 104 is smaller than the angles between the incident direction of the ions I1 and I2 of FIGS. 6A and 6B and the normal line of the top surface of the epitaxy layer 104.

Figure 14:
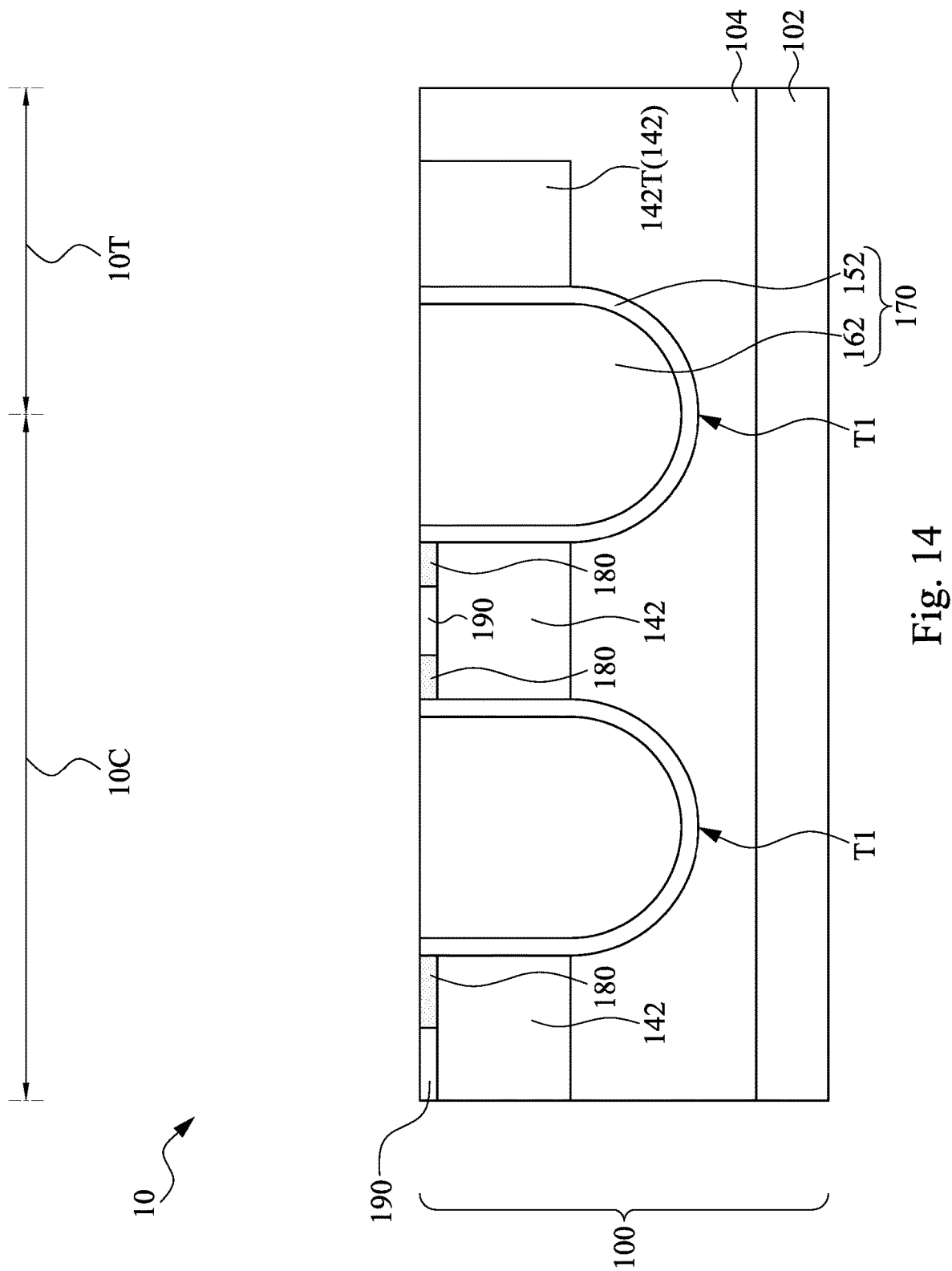

Reference is made to FIG. 14. The patterned mask M3 is moved. A semiconductor device 10 is therefore formed. In some embodiments, the semiconductor device 10 is a metal oxide silicon field effect transistor (MOSFET) device. Because the gate structures 170 are formed in the trenches T1 of the epitaxy layer 104, the semiconductor device 10 can also be referred to as a trench MOSFET. In some other embodiments, the semiconductor device 10 can also be referred to as a UMOS (U-shaped trench MOSFET).

It is noted that the P-well regions 142 has a portion 142T, in which the portion 142T of the P-well regions 142 are protected by the patterned masks M2 and M3 during the processes of FIGS. 12 and 13. In some embodiments, the portion 142T of the P-well regions 142 is within a terminal region 10T of the semiconductor device 10. The terminal region 10T can be regarded as a region at a boundary of the semiconductor device 10. Typically, this region of the semiconductor device 10 does not have circuit function, and thus the portion 142T of the P-well regions 142 within this region does not undergo the implantation process of FIGS. 12 and 13. On the other hand, the other portions within a cell region 10C of the semiconductor device 10 may undergo the implantation process of FIGS. 12 and 13. The cell region 10C can be regarded as a region of semiconductor device 10 that performs certain functional operations.

Figure 15A:
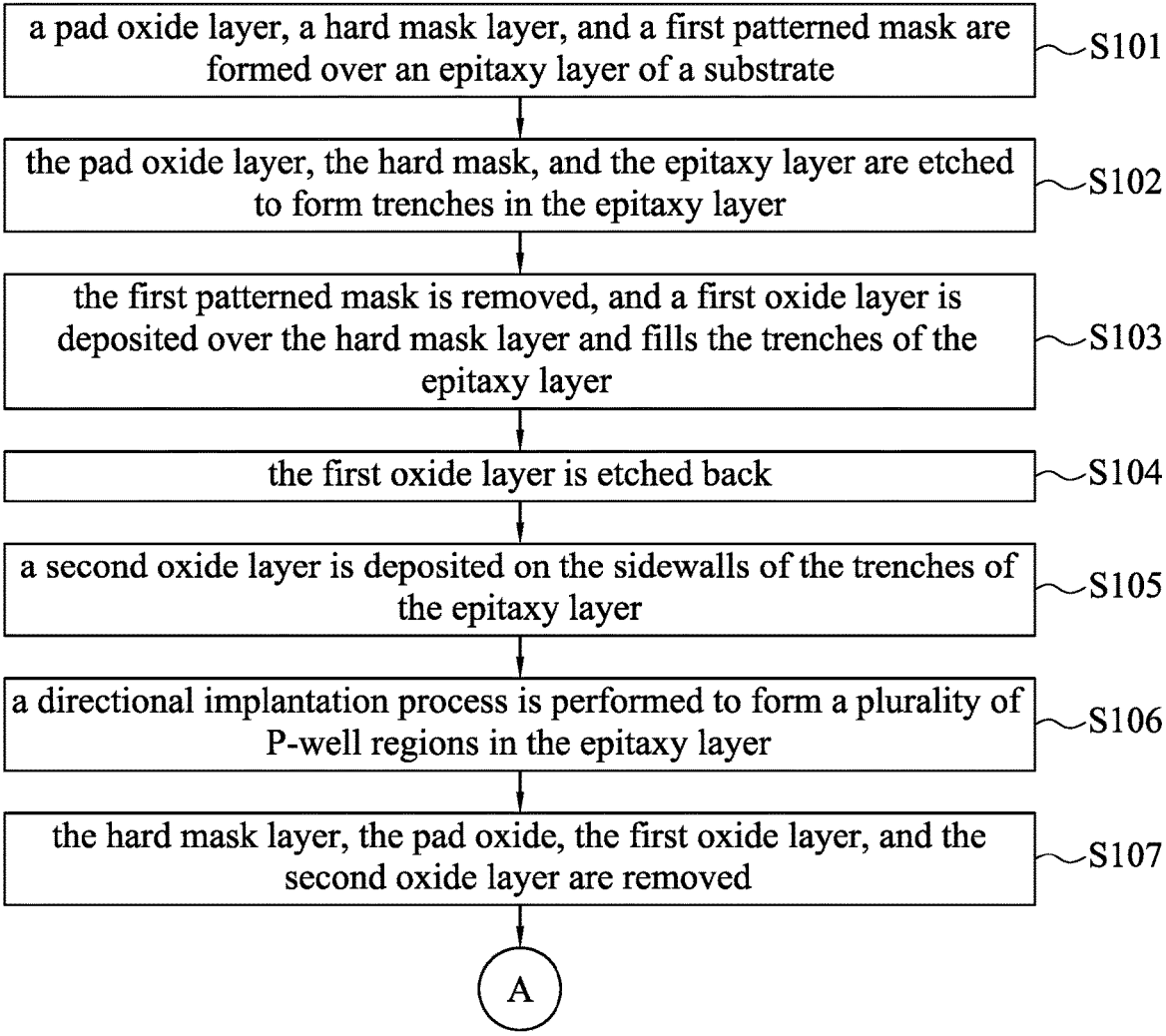
FIGS. 15A and 15B illustrate a method for forming a semiconductor device in accordance with some embodiments of the present disclosure.
Figure 15B:
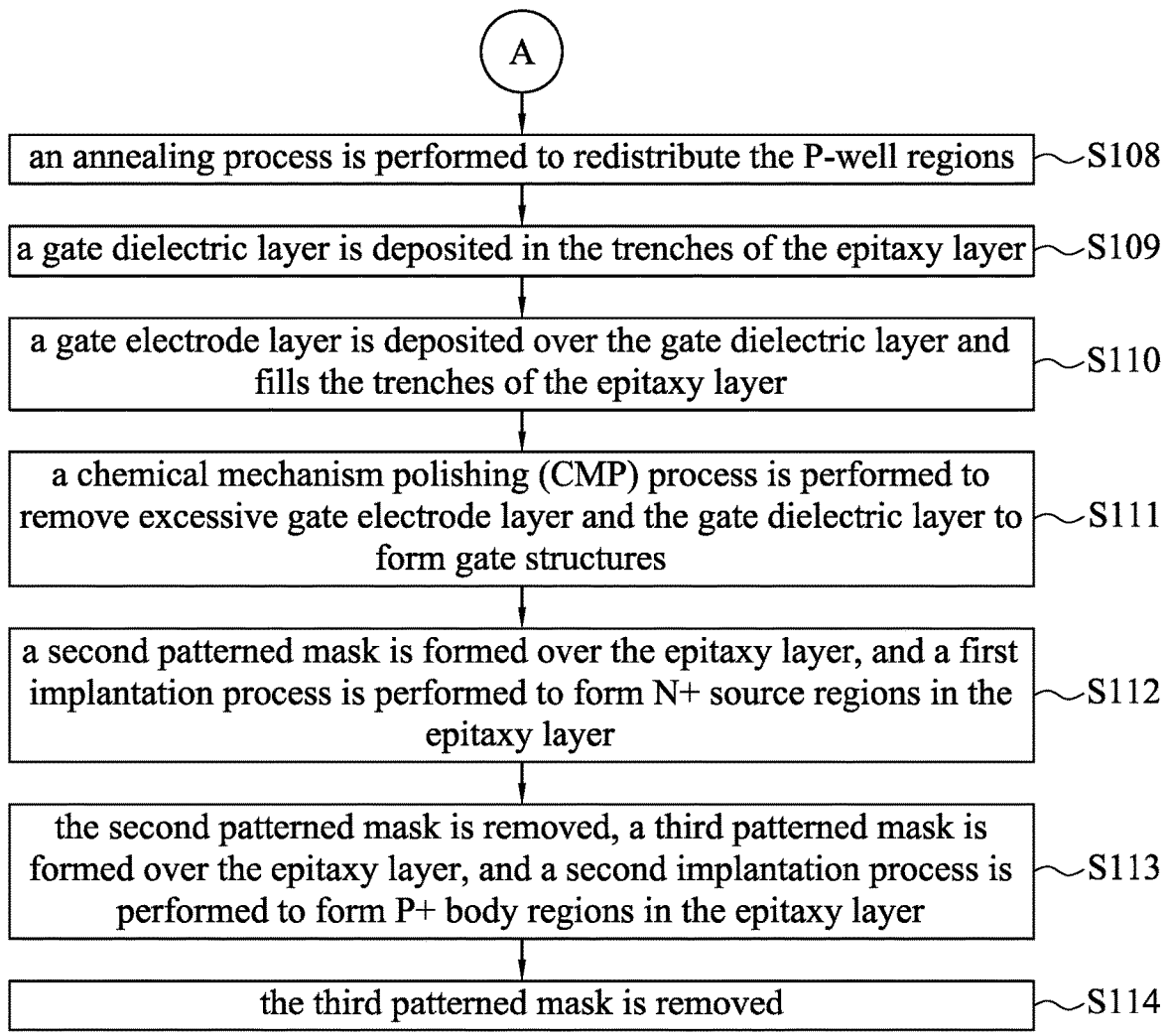

FIGS. 15A and 15B illustrate a method 1000 of manufacturing in accordance with some embodiments of the present disclosure. Although the method 1000 is illustrated and/or described as a series of acts or events, it will be appreciated that the method is not limited to the illustrated ordering or acts. Thus, in some embodiments, the acts may be carried out in different orders than illustrated, and/or may be carried out concurrently. Further, in some embodiments, the illustrated acts or events may be subdivided into multiple acts or events, which may be carried out at separate times or concurrently with other acts or sub-acts. In some embodiments, some illustrated acts or events may be omitted, and other un-illustrated acts or events may be included.

At block S101, a pad oxide layer, a hard mask layer, and a first patterned mask are formed over an epitaxy layer of a substrate. FIG. 1 illustrates a schematic view of some embodiments corresponding to act in block S101.

At block S102, the pad oxide layer, the hard mask, and the epitaxy layer are etched to form trenches in the epitaxy layer. FIG. 2 illustrates a schematic view of some embodiments corresponding to act in block S102.

At block S103, the first patterned mask is removed, and a first oxide layer is deposited over the hard mask layer and fills the trenches of the epitaxy layer. FIG. 3 illustrates a schematic view of some embodiments corresponding to act in block S103.

At block S104, the first oxide layer is etched back. FIG. 4 illustrates a schematic view of some embodiments corresponding to act in block S104.

At block S105, a second oxide layer is deposited on the sidewalls of the trenches of the epitaxy layer. FIGS. 5A and 5B illustrate schematic views of some embodiments corresponding to act in block S105.

At block S106, a directional implantation process is performed to form a plurality of P-well regions in the epitaxy layer. FIGS. 6A and 6B illustrate schematic views of some embodiments corresponding to act in block S106.

At block S107, the hard mask layer, the pad oxide layer, the first oxide layer, and the second oxide layer are removed. FIG. 7 illustrates a schematic view of some embodiments corresponding to act in block S107.

At block S108, an annealing process is performed to redistribute the P-well regions. FIG. 8A illustrates a schematic view of some embodiments corresponding to act in block S108.

At block S109, a gate dielectric layer is deposited in the trenches of the epitaxy layer. FIG. 9 illustrates a schematic view of some embodiments corresponding to act in block S109.

At block S110, a gate electrode layer is deposited over the gate dielectric layer and fills the trenches of the epitaxy layer. FIG. 10 illustrates a schematic view of some embodiments corresponding to act in block S110.

At block S111, a chemical mechanism polishing (CMP) process is performed to remove excessive gate electrode layer and the gate dielectric layer to form gate structures. FIG. 11 illustrates a schematic view of some embodiments corresponding to act in block S111.

At block S112, a second patterned mask is formed over the epitaxy layer, and a first implantation process is performed to form N+ source regions in the epitaxy layer. FIG. 12 illustrates a schematic view of some embodiments corresponding to act in block S112.

At block S113, the second patterned mask is removed, a third patterned mask is formed over the epitaxy layer, and a second implantation process is performed to form P+ body regions in the epitaxy layer. FIG. 13 illustrates a schematic view of some embodiments corresponding to act in block S113.

At block S114, the third patterned mask is removed. FIG. 14 illustrates a schematic view of some embodiments corresponding to act in block S114.

Figure 16:
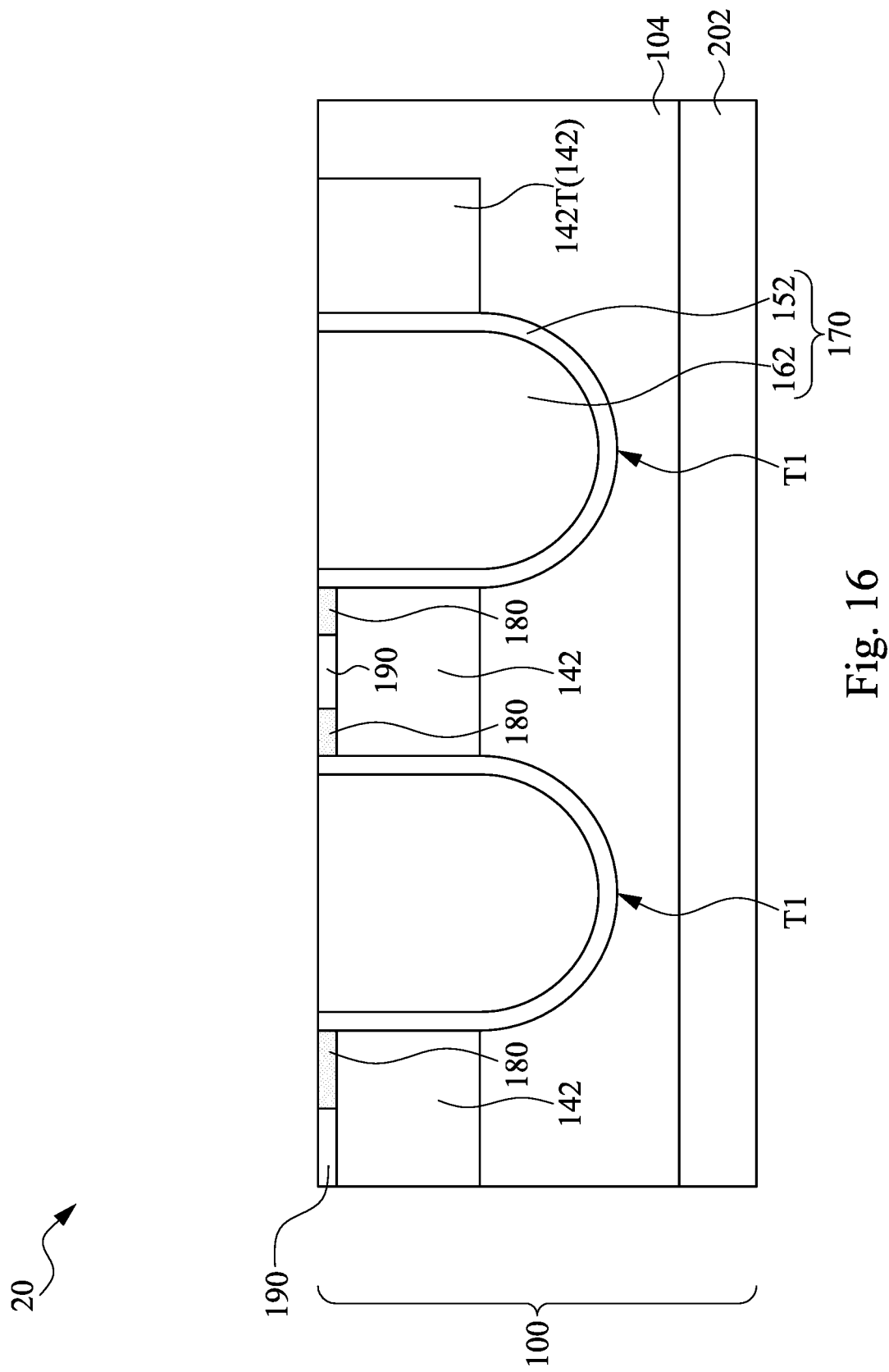
FIG. 16 is a cross-sectional view of a semiconductor device in accordance with some embodiments of the present disclosure.

Reference is made to FIG. 16. FIG. 16 is a semiconductor device in accordance with some embodiments of the present disclosure. The semiconductor device in FIG. 16 is different from the semiconductor device in FIG. 14, in that the semiconductor region 202 in FIG. 16 is a P-type region. In some embodiments, semiconductor region 202 is a heavily doped layer doped with a p-type impurity such as boron (B), gallium (Ga), indium (In), aluminium (Al), for example, to an impurity concentration between about $10^{19}/cm^3$ and about $10^{21}/cm^3$. In the described embodiments, the term "heavily doped" means an impurity concentration of above about $10^{19}/cm^3$. The semiconductor device in FIG. 16 can be regarded as an insulated gate bipolar transistor (IGBT). In some embodiments, some elements of FIG. 16 are similar or the same as those described in FIGS. 1-14, and thus such elements are labeled the same, and will not be repeated for brevity.

FIGS. 17 to 23 are cross-sectional views of a semiconductor device in various stages of fabrication in accordance with some embodiments of the present disclosure.

Figure 17:
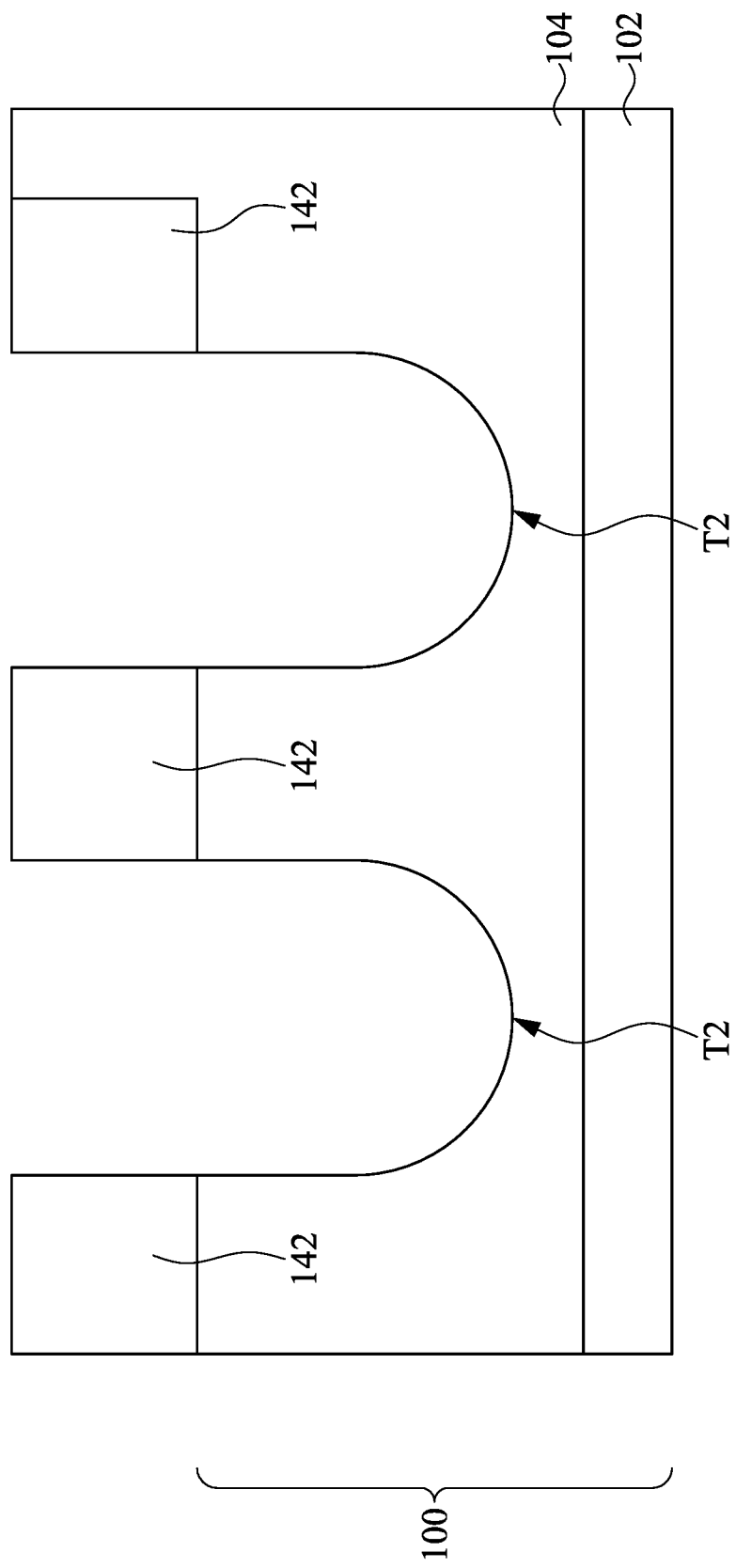
FIGS. 17 to 23 are cross-sectional views of a semiconductor device in various stages of fabrication in accordance with some embodiments of the present disclosure.

Reference is made to FIG. 17. The structure of FIG. 17 is similar to the structure as described in FIGS. 8A and 8B. Some elements of FIG. 17 are the same or similar to the elements of FIG. 8A, and thus such elements are labeled the same and the structural details will not be repeated for brevity. FIG. 17 is different from FIG. 8A, in that trenches T2 of the epitaxy layer 104 are deeper than the trenches T1 in FIG. 8A. In some embodiments, the P-well regions 142 of FIG. 17 are formed by the same or similar method as described with respect to FIGS. 3 to 8B, and thus relevant details are not repeated.

Figure 18:
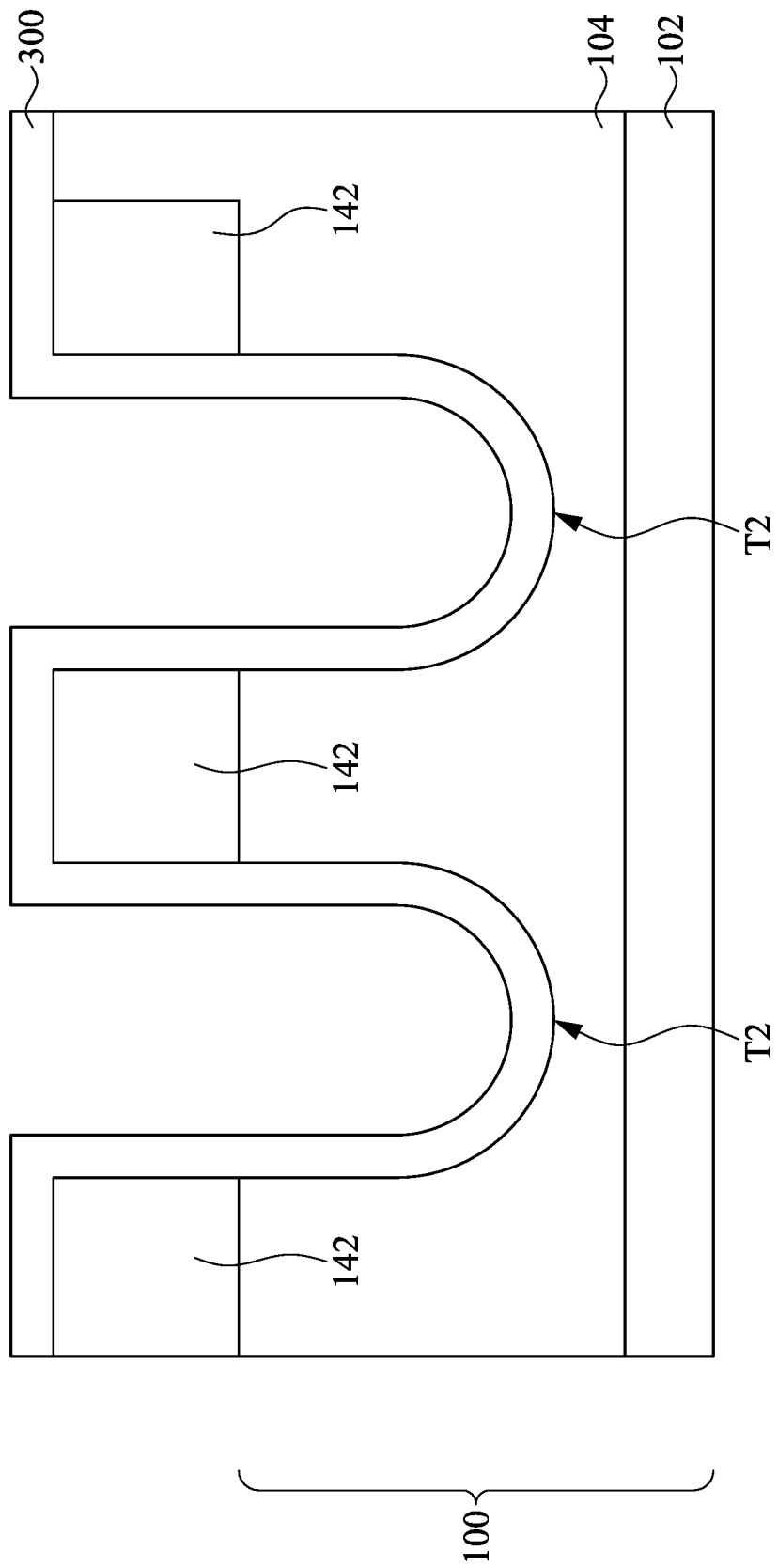

Reference is made to FIG. 18. A gate dielectric layer 300 is formed over the epitaxy layer 104 and in the trenches T2. The gate dielectric layer 300 lines the trenches T2. The gate dielectric layer 300 may be oxide layer, such as silicon oxide, silicon dioxide ($SiO_2$). In some embodiments, the gate dielectric layer 300 can be formed by suitable process, such as CVD, ALD, or thermal oxidation process. In some embodiments, the gate dielectric layer 300 is grown to have a desired thickness based on device optimization for low Rds and high breakdown voltage. The thick gate dielectric layer 300 here reduces the silicon surface electric field, allowing the use of higher doping and leading to lower Rds for the same breakdown rating.

Figure 19:
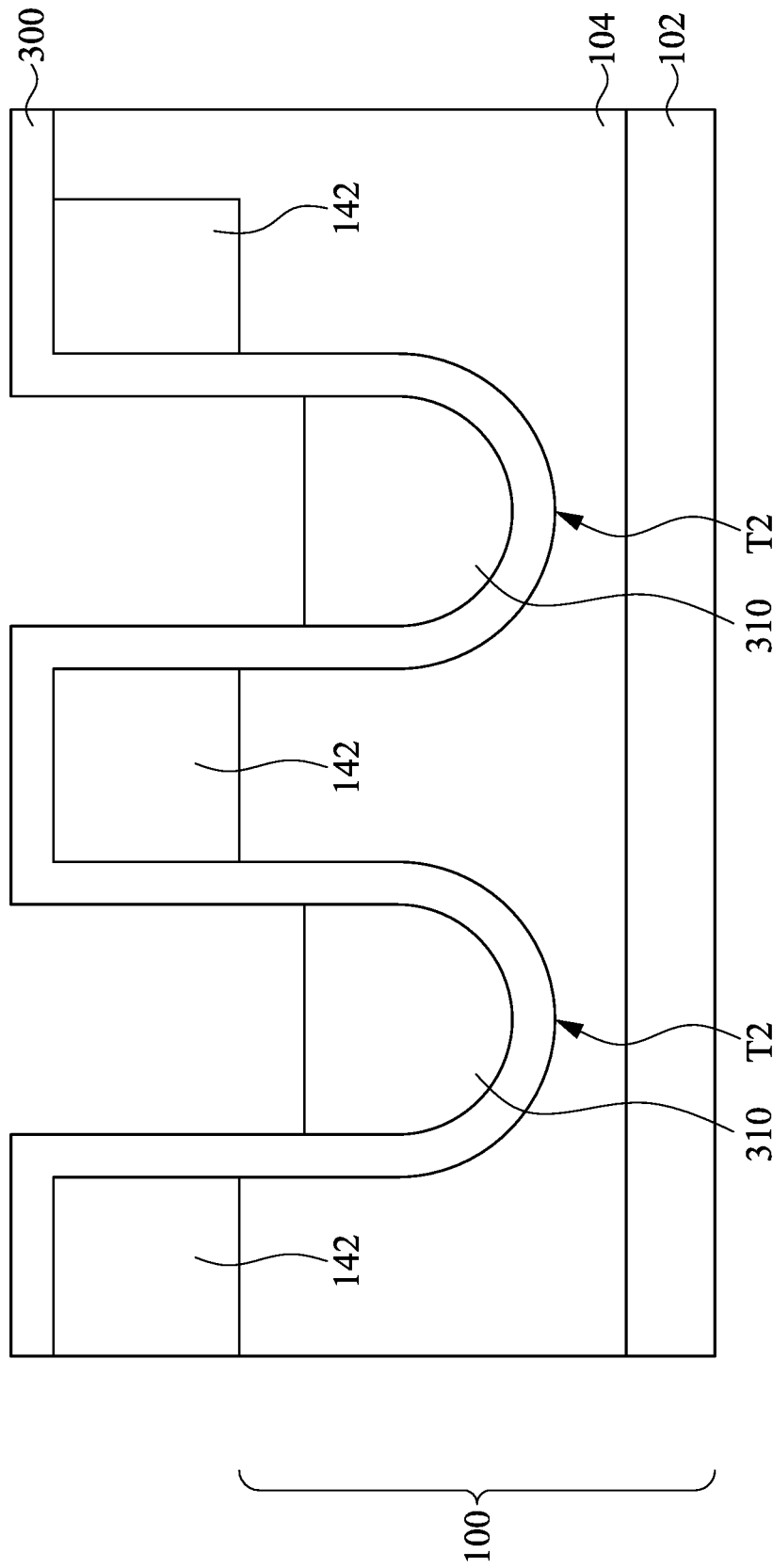

Reference is made to FIG. 19. A plurality of gate electrodes 310 is formed in the trenches T2 and over the gate dielectric layer 300. In some embodiments, the gate electrodes 310 may be polysilicon. In some embodiments, the gate electrodes 310 can be formed by, for example, depositing a blanket gate electrode layer over the epitaxy layer 104 and fills the trenches T2, followed by an etching back process to lower top surface of the gate electrode layer using an etchant that etches gate electrode material (e.g., polysilicon) at a faster etch rate than etching gate dielectric material (e.g., silicon oxide). In some embodiments, the etching back process is performed to the gate electrode layer such that the top surface of the gate electrodes 310 is lower than the topmost surface of the epitaxy layer 104. In some other embodiments, the etching back process is performed to the gate electrode layer such that the top surface of the gate electrodes 310 is lower than the bottommost end of the P-well regions 142.

Figure 20:
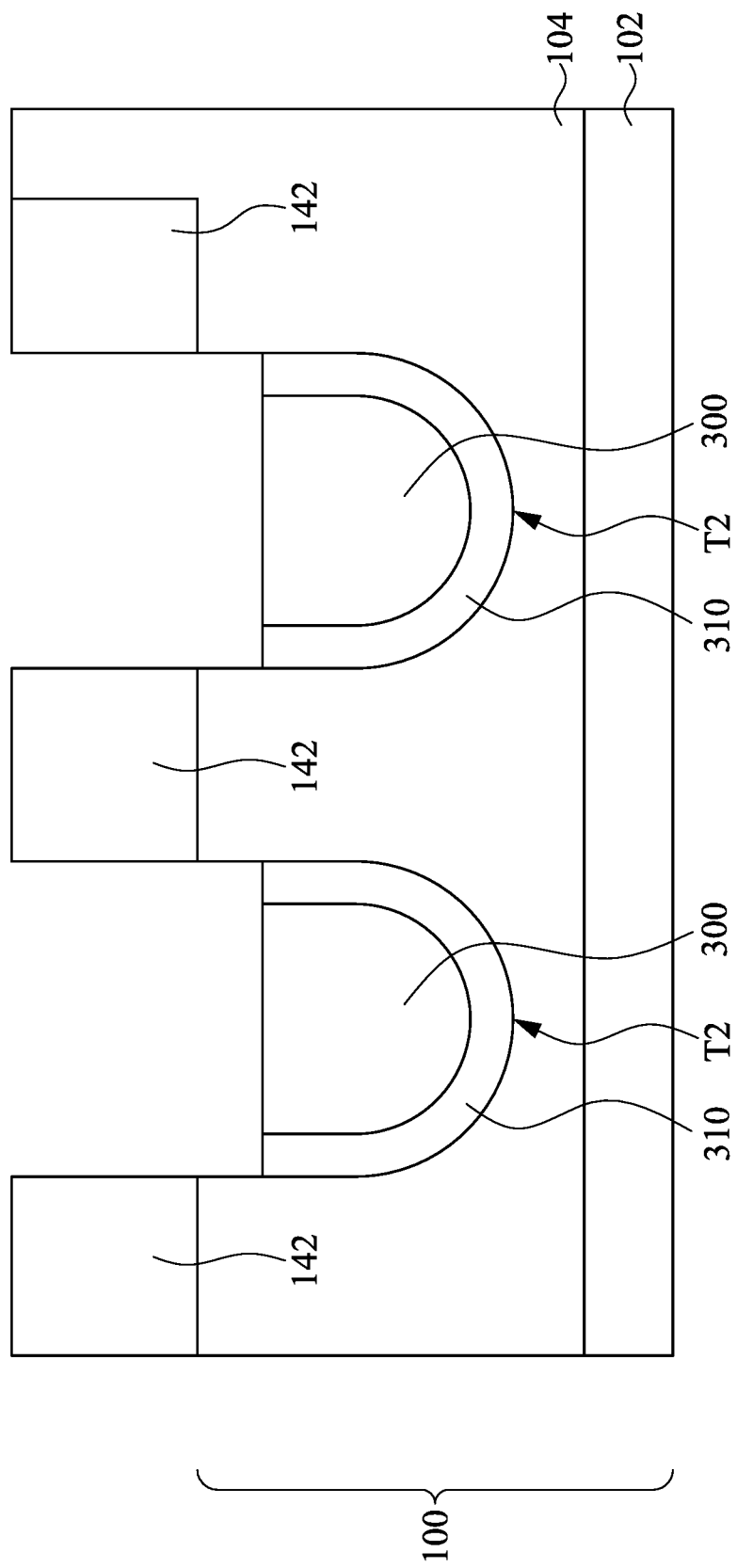

Reference is made to FIG. 20. Portions of the gate dielectric layer 300 are removed using, for example, a wet etch, until the top surface and sidewalls of the epitaxy layer 104 are clear in the area not encapsulated by the gate electrodes 310. In some embodiments, the etching process is performed such that the portions of the gate dielectric layer 300 within the lower portion of trenches T2 are not etched. That is, at least portions of the gate dielectric layer 300 remain between the gate electrodes 310 and the epitaxy layer 104 after the etching process. The etching process may be, for example, a selective etching process using an etchant (e.g., diluted HF) that etches the gate dielectric material (e.g., silicon oxide) than epitaxy materials in the layer 104 (e.g., single crystalline silicon) and gate electrode materials (e.g., polysilicon).

Figure 21:
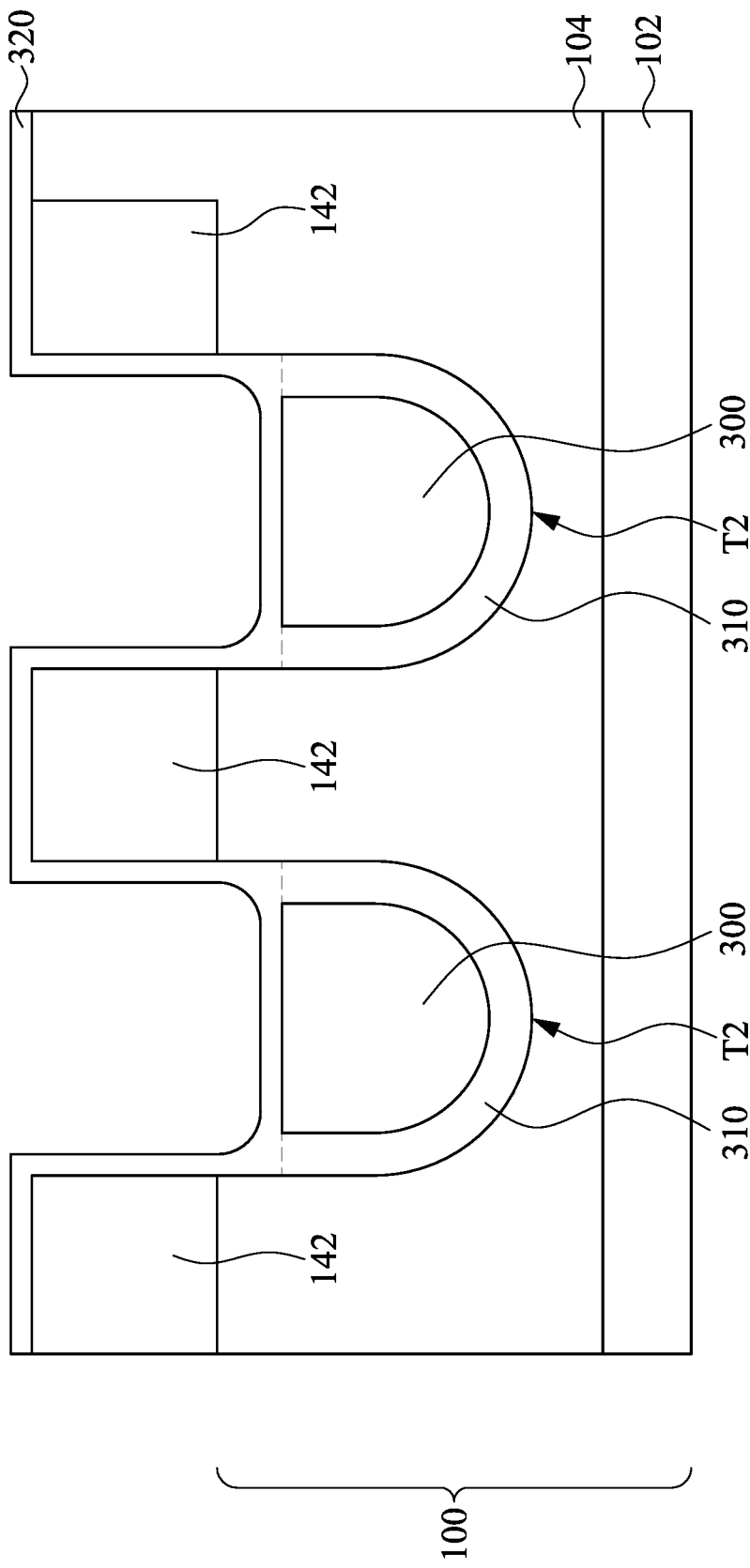

Reference is made to FIG. 21. A gate dielectric layer 320 is formed over the gate electrodes 310 and along the exposed surfaces of the epitaxy layer 104. In some embodiments, the gate dielectric layer 320 is formed to cover and seal the gate electrodes 310. In some embodiments, the gate electrodes 310 can be interchangeably referred to as bottom-shielding electrodes 310. In some embodiments, the gate dielectric layer 320 is thinner than the gate dielectric layer 300 formed in FIG. 18. The thin gate dielectric layer 320 on the gate trench sidewall provides the advantage of reducing gate threshold voltage.

Figure 22:
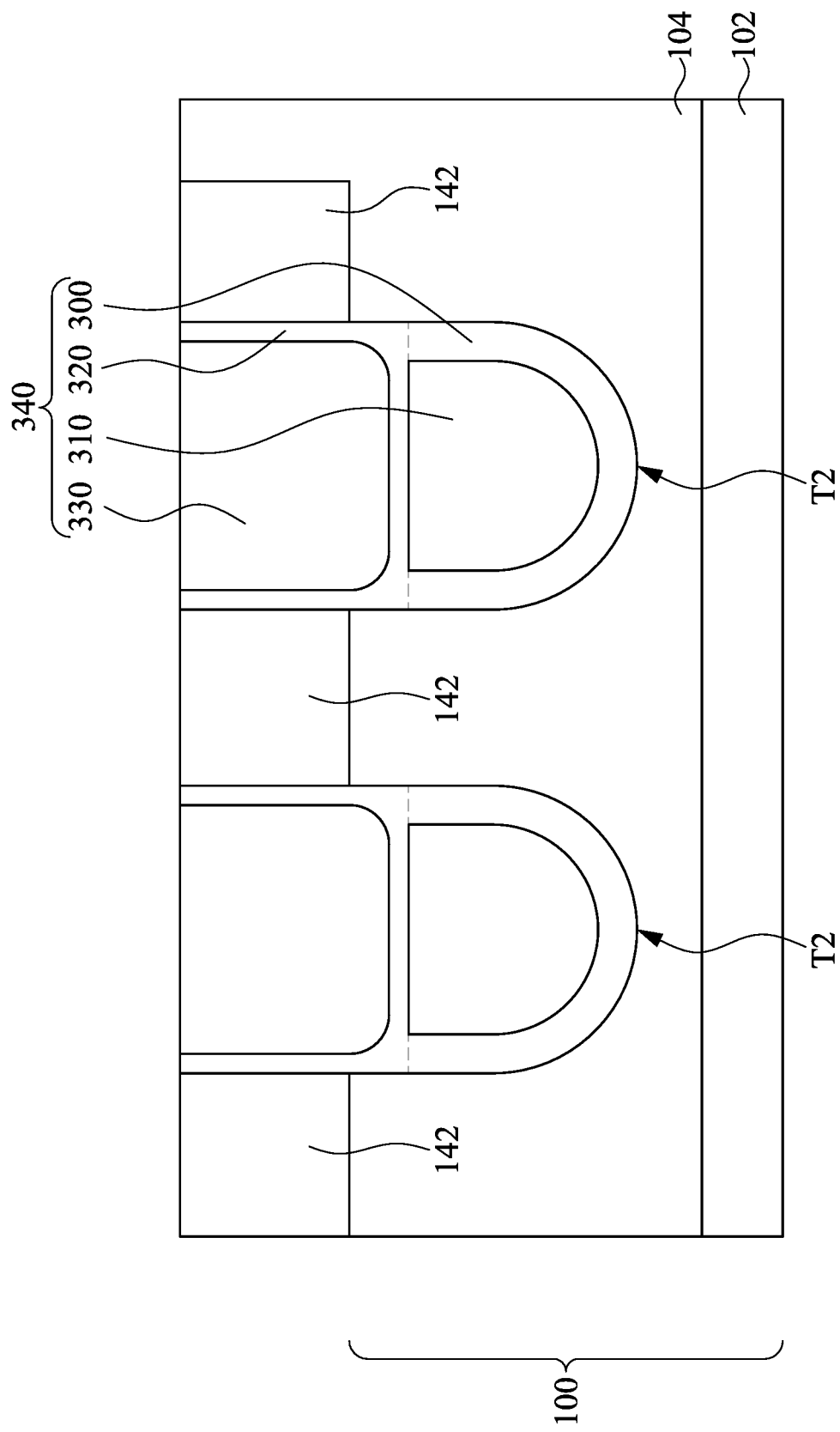

Reference is made to FIG. 22. A plurality of gate electrodes 330 are formed in the trenches T2 of the epitaxy layer 104. In some embodiments, the gate electrodes 330 may be polysilicon. In some embodiments, the gate electrodes 330 can be formed by, for example, depositing a blanket gate electrode layer over the epitaxy layer 104 and fills the trenches T2, followed by a CMP process to remove excessive gate electrode layer until the top surface of the epitaxy layer 104 is exposed. In some embodiments, in each trench T2, the remaining gate dielectric layer 300, the gate electrode 310, the remaining gate dielectric layer 320, and the gate electrode 330 can be collectively referred to as a gate structure 340.

Figure 23:
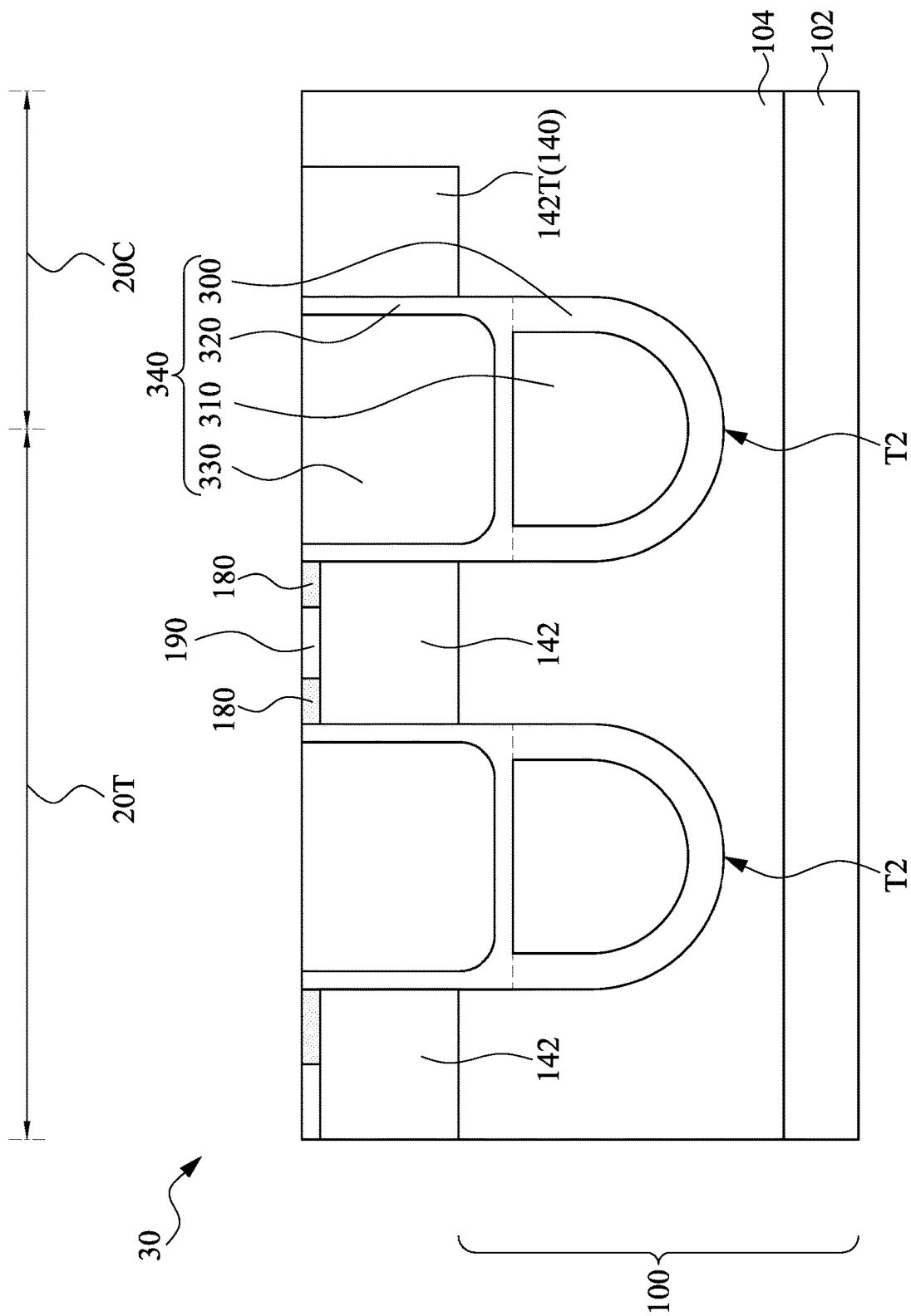

Reference is made to FIG. 23. N+ source regions 180 and P+ body regions 190 are formed in the epitaxy layer 104, and a semiconductor device 20 is formed. In some embodiments, semiconductor device 20 of FIG. 23 can be referred to as a shielded-gate trench (SGT) FETs. Typically, SGT FETs include a shielding electrode (e.g., the gate electrode 320) under a gate electrode (e.g., the gate electrode 330). The shielding gate (e.g., the gate electrode 320) and the gate electrode (e.g., the gate electrode 330) are insulated from each other by a dielectric layer (e.g., the gate dielectric layer 320) serving as an interelectrode dielectric.

In some embodiments, the semiconductor device 20 includes a cell region 20C and a terminal region 20T, which are similar to the cell region 10C and the terminal region 10T of the semiconductor device 10 described in FIG. 14. The N+ source regions 180 and the P+ body regions 190 are formed with similar or the same method as discussed in FIGS. 12 to 14, and thus relevant details will not be repeated for brevity.

Figure 24:
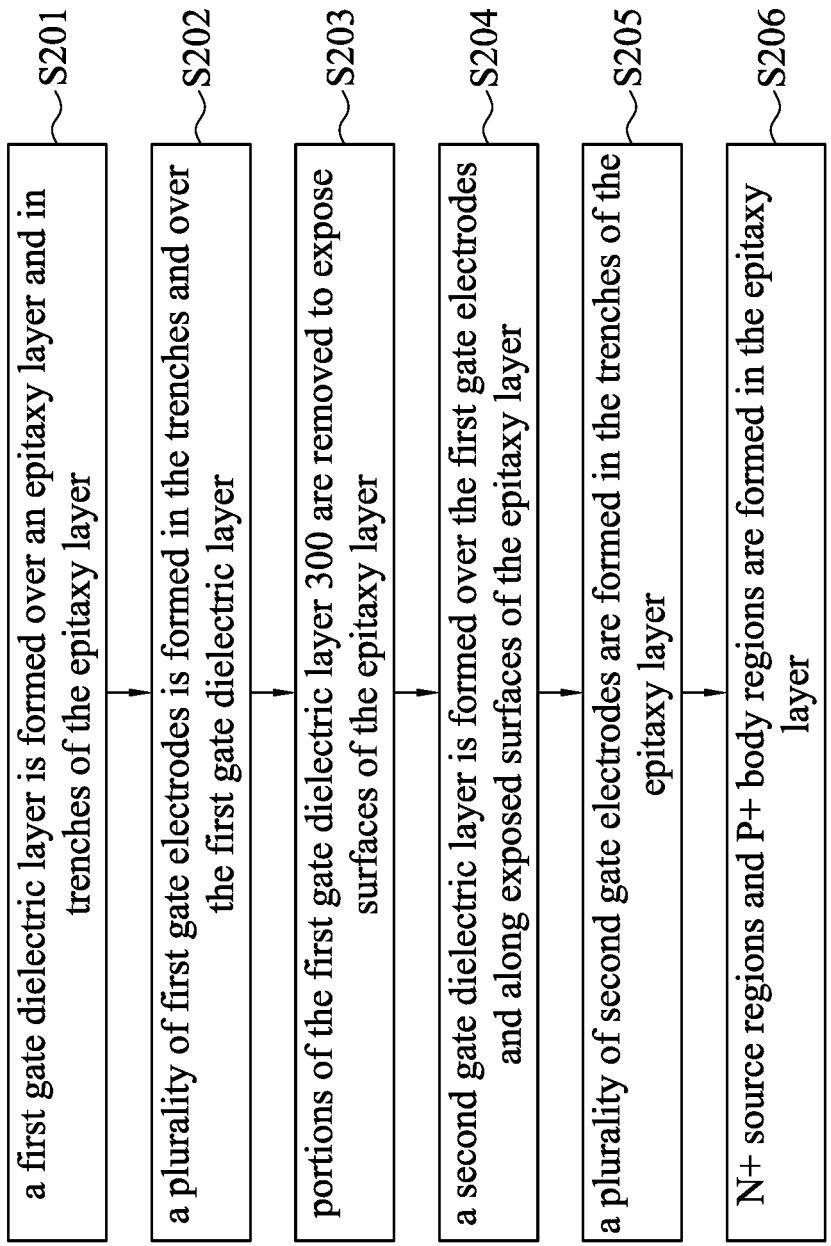
FIG. 24 is a method for forming a semiconductor device in accordance with some embodiments of the present disclosure.

FIG. 24 is a method for forming a semiconductor device in accordance with some embodiments of the present disclosure. Although the method 2000 is illustrated and/or described as a series of acts or events, it will be appreciated that the method is not limited to the illustrated ordering or acts. Thus, in some embodiments, the acts may be carried out in different orders than illustrated, and/or may be carried out concurrently. Further, in some embodiments, the illustrated acts or events may be subdivided into multiple acts or events, which may be carried out at separate times or concurrently with other acts or sub-acts. In some embodiments, some illustrated acts or events may be omitted, and other un-illustrated acts or events may be included.

In some embodiments, some operations can be performed prior to blocks S201 of method 2000, such as operations described in blocks S101 to S108 with respect to FIGS. 1 to 8B. Accordingly, FIG. 17 illustrates an initial structure of block S201 of method 2000.

At block S201, a first gate dielectric layer is formed over an epitaxy layer and in trenches of the epitaxy layer. FIG. 18 illustrates a schematic view of some embodiments corresponding to act in block S201.

At block S202, a plurality of first gate electrodes is formed in the trenches and over the first gate dielectric layer. FIG. 19 illustrates a schematic view of some embodiments corresponding to act in block S202.

At block S203, portions of the first gate dielectric layer 300 are removed to expose surfaces of the epitaxy layer. FIG. 20 illustrates a schematic view of some embodiments corresponding to act in block S203.

At block S204, a second gate dielectric layer is formed over the first gate electrodes and along exposed surfaces of the epitaxy layer. FIG. 21 illustrates a schematic view of some embodiments corresponding to act in block S204.

At block S205, a plurality of second gate electrodes are formed in the trenches of the epitaxy layer. FIG. 22 illustrates a schematic view of some embodiments corresponding to act in block S205.

At block S206, N+ source regions and P+ body regions are formed in the epitaxy layer. FIG. 23 illustrates a schematic view of some embodiments corresponding to act in block S206.

Based on the above discussion, it can be seen that the present disclosure offers advantages. It is understood, however, that other embodiments may offer additional advantages, and not all advantages are necessarily disclosed herein, and that no particular advantages are required for all embodiments. One advantage is that a hard mask layer is used for patterning an epitaxy layer to form trenches in the epitaxy layer. Then, the P-well regions can be formed, using the same hard mask layer, in the epitaxy layer via a directional implantation process. The P-well regions are formed in the regions of the epitaxy layer underlying the hard mask layer, and thus the P-well regions can be regarded as substantially self-aligned with the hard mask layer, and thus an additional mask used to define the positions of the P-well regions can be omitted, which will reduce process cost and process time.

In some embodiments of the present disclosure, a semiconductor device includes substrate, a first gate structure and a second gate structure. The substrate has a semiconductor region and an epitaxy layer over the semiconductor region. The first gate structure and the second gate structure are disposed in the epitaxy layer, the first gate structure and the second gate structure have rounded bottom surface, in which the epitaxy layer has a P-well region laterally between the first gate structure and the second gate structure, and a dopant concentrations in the P-well region varies along a direction from the first gate structure to the second gate structure.

In some embodiments of the present disclosure, a semiconductor device includes substrate, a first gate structure, a second gate structure, and an epitaxy layer. The first gate structure and the second gate structure are over the substrate, in which the first gate structure and the second gate structure each comprises a shielding electrode, a gate electrode over the shielding electrode, and a first gate dielectric layer vertically separating the shielding electrode from the gate electrode. The epitaxy layer is over the substrate and cups an underside of the first gate structure and the second gate structure, in which the epitaxy layer comprises a doped region laterally between the first gate dielectric layer of the first gate structure and the first gate dielectric layer of the second gate structure, a dopant concentration of the doped region being non-uniform along a lateral direction.

In some embodiments of the present disclosure, a semiconductor device includes substrate, a first gate structure, a second gate structure, and an epitaxy layer. The first gate structure and the second gate structure are over the substrate. The epitaxy layer is over the substrate and laterally surrounds the first gate structure and the second gate structure, in which the epitaxy layer comprises a P-well region between the first gate structure and the second gate structure, wherein the P-well region comprises a first portion adjacent the first gate structure, a second portion adjacent the second gate structure, and a middle portion between the first and second portions, and the P-well region has a dopant concentration decreasing from the first portion to the middle portion and increasing from the middle portion to the second portion. The epitaxy layer further comprises N-doped regions over the first and second portions of the P-well region, respectively, and a P-doped region over the middle portion of the P-well region and having a dopant concentration greater than the middle portion of the P-well region.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A semiconductor device, comprising:
    a substrate; and
    a first gate structure and a second gate structure disposed in the substrate, wherein the substrate has a doped region laterally between the first gate structure and the second gate structure, and wherein along a topmost portion of the doped region, a dopant concentration in the doped region varies along a direction from the first gate structure to the second gate structure.

2. The semiconductor device of claim 1, wherein along the direction from the first gate structure to the second gate structure, the doped region has:
    a first dopant concentration at a first side of the doped region near the first gate structure;
    a second dopant concentration at a second side of the doped region near the second gate structure; and
    a third dopant concentration at a middle of the doped region, wherein the first and second dopant concentrations are higher than the third dopant concentration.

3. The semiconductor device of claim 2, wherein the doped region is a P-type doped region.

4. The semiconductor device of claim 1, wherein the first gate structure and the second gate structure each includes a rounded bottom surface.

5. The semiconductor device of claim 1, wherein the first gate structure comprises a gate dielectric in contact with the doped region.

6. The semiconductor device of claim 5, wherein the gate dielectric has a U-shaped cross-sectional profile.

7. The semiconductor device of claim 1, wherein top surfaces of the first gate structure and the second gate structure are substantially level with a top surface of the substrate.

8. A semiconductor device, comprising:
    a substrate; and
    a first gate structure and a second gate structure disposed in the substrate, wherein
    the substrate has a doped region laterally between the first gate structure and the second gate structure, and wherein along a topmost portion of the doped region, a middle portion of the doped region has a lower dopant concentration than dopant concentrations of portions of the doped region on opposite sides of the middle portion.

9. The semiconductor device of claim 8, wherein the doped region is a P-well region.

10. The semiconductor device of claim 8, wherein the first gate structure and the second gate structure each includes a rounded bottom surface.

11. The semiconductor device of claim 8, wherein the first gate structure comprises a gate dielectric in contact with the doped region and having a U-shaped cross-sectional profile.

12. The semiconductor device of claim 8, wherein a top surface of the first gate structure is substantially level with a top surface of the substrate.

13. The semiconductor device of claim 8, wherein a bottom end of the first gate structure is lower than a bottom end of the doped region.

14. The semiconductor device of claim 8, wherein the first and second gate structures each comprises:
    a shielding electrode;
    a gate electrode over the shielding electrode;
    a first gate dielectric layer cupping the shielding electrode; and
    a second gate dielectric layer vertically separating the shielding electrode from the gate electrode.

15. A semiconductor device, comprising:
    a substrate;
    a gate structure in the substrate; and
    a first doped region and a second doped region in the substrate and on opposite sides of the gate structure, wherein along a topmost portion of the first doped region, a dopant concentration of the first doped region varies along a horizontal direction.

16. The semiconductor device of claim 15, wherein the first doped region comprises a first portion adjacent to the gate structure, a second portion, and a middle portion between the first and second portions, and the dopant concentration of the first doped region decreases from the first portion to the middle portion and increases from the middle portion to the second portion.

17. The semiconductor device of claim 15, wherein the first and second doped regions are both P-well regions.

18. The semiconductor device of claim 17, further comprising:
    a heavily doped N-type region over the first doped region; and
    a heavily doped P-type region over the first doped region, wherein the heavily doped N-type region is between the heavily doped P-type region and the gate structure.

19. The semiconductor device of claim 18, wherein the heavily doped N-type region is over the topmost portion of the first doped region, wherein a topmost surface of the second doped region is free of a dopant of the heavily doped N-type region.

20. The semiconductor device of claim 15, wherein the gate structure comprises:
    a shielding electrode;
    a gate electrode over the shielding electrode;
    a first gate dielectric layer cupping the shielding electrode; and
    a second gate dielectric layer vertically separating the shielding electrode from the gate electrode.

* * * * *